(12) United States Patent
Ishigai et al.

(10) Patent No.: US 7,019,146 B1
(45) Date of Patent: Mar. 28, 2006

(54) FERROCENE COMPOUND AND USE THEREOF

(75) Inventors: Masaki Ishigai, Gotenba (JP); Naoaki Murao, Gotenba (JP); Nobuo Sekiguchi, Gotenba (JP); Tadakatsu Takahashi, Gotenba (JP)

(73) Assignee: Chugai Seiyaku Kabushiki Kaisya, Tokyo (JP)

( * ) Notice: Subject to any disclaimer, the term of this patent is extended or adjusted under 35 U.S.C. 154(b) by 0 days.

(21) Appl. No.: 10/519,629

(22) PCT Filed: Jun. 27, 2003

(86) PCT No.: PCT/JP03/08166

§ 371 (c)(1), (2), (4) Date: Dec. 23, 2004

(87) PCT Pub. No.: WO2004/002996

PCT Pub. Date: Jan. 8, 2004

(30) Foreign Application Priority Data

Jun. 27, 2002 (JP) .............................. 2002-188541

(51) Int. Cl.
*C07F 17/02* (2006.01)
*A61K 31/59* (2006.01)

(52) U.S. Cl. ...................... 548/103; 556/144; 514/167; 514/502

(58) Field of Classification Search ................ 556/144; 548/103; 514/167, 502
See application file for complete search history.

(56) References Cited

FOREIGN PATENT DOCUMENTS

JP 4-5287 1/1992

OTHER PUBLICATIONS

"The structure of bicyclic ferrocenylmethylene substituted 2-pyrazolines and their reactions with azodicarboxylic acid N-phenylimide" by Klimova et al., Journal of Organometallic Chemistry 585 (1999) pp. 106-114.

(Continued)

*Primary Examiner*—Porfirio Nazario-Gonzalez
(74) *Attorney, Agent, or Firm*—Darby & Darby

(57) ABSTRACT

The present invention provides a novel ferrocene compound; a reagent containing the compound; a high-sensitivity method of measuring a vitamin D compound using the reagent; etc. Specifically, a ferrocene compound represented by the following formula (1):

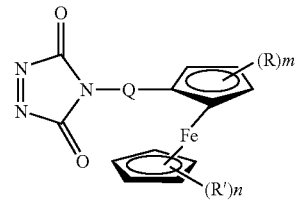

is reacted with a vitamin D compound and the combined compound of these compounds is subjected to LC/ESI-MS/MS. Thus, the VD compound can be measured with higher sensitivity than in conventional techniques. The ferrocene compound of the present invention is extremely useful as a derivatization agent when a VD compound is measured by LC/ESI-MS/MS. The obtained compound wherein the ferrocene compound and the VD compound have been combined with each other, is useful as, e.g., a labeled compound, when the VD compound is measured by LC/ESI-MS/MS.

28 Claims, 12 Drawing Sheets

OTHER PUBLICATIONS

"Liquid chromatography-mass spectrometric method combined with derivatization for determination of 1α—hydroxyvitamin $D_3$ in human plasma" by Higashi et al., Journal of Chromatography B, 772 (2002) pp. 229-238.

"Synthesis of a Reagent for Fluorescence-Labeling of Vitamin D and Its Use in Assaying Vitamin D Metabolites" by Shimizu et al., Analytical Biochemistry 194, pp77-81 (1991).

"Derivatization in LC/MS" by Mitamura et al., Yakugaku Zasshi, 118(6), pp206-215 (1998).

"Development of Analysis of Vitamin D Metabolites" by Higashi et al, Yakugaku Zasshi 119(12) pp. 898-920 (1999).

"On-line Post-column Diels-Alder Derivatization for the Determination of Vitamin D3 and its Metabolites by Liquid Chromatography/Thermospray Mass Spectrometry" by Vreeken t al., Biological Mass Spectrometry, vol. 22, pp. 621-632 (1993).

"Characterization of vitamin D3 metabolites using continuous-flow fast atom bombardment tandem mass spectrometry and high-performance liquid chromatography" by Yeung et al., Journal of Chromatography, 645 (1993) pp. 115-123.

"An Electron-Capture Dienophile Derivatization Agent for Increasing Sensitivity: Determination of a Vitamin D Analog (Ro 24-2090) in Plasma Samples with Liquid Chromatography/Mas Spectrometry" by Wang et al., Analytical Biochemistry 243, pp 28-40 (1996).

"Derivatization for Electrospray Ionization Mass Spectrometry. 3. Electrochmically Ionizable Derivatives" by Berkel et al., Anal. Chem. 1998, 70, pp. 1544-1554.

FERROCENE COMPOUND AND USE THEREOF

CROSS-REFERENCE TO PRIOR APPLICATION

This is a U.S. national phase application under 35 U.S.C. §371 of International Patent Application No. PCT/JP2003/008166 filed Jun. 27, 2003, and claims the benefit of Japanese Patent Application No. 2002-188541 filed Jun. 27, 2002 both of which are incorporated by reference herein. The International Application was published in Japanese on Jan. 8, 2004 as WO 2004/002996 A1 under PCT Article 21(2).

TECHNICAL FIELD OF THE INVENTION

The present invention provides a novel ferrocene compound, a reagent comprising the compound, a high-sensitivity method of measuring a vitamin D compound using the reagent, and a combined compound of the ferrocene compound and a vitamin D compound.

BACKGROND OF THE INVENTION

At present, various compounds such as calcitriol (trade name: Rocaltrol (registered trademark)), alfacalcidol (trade name: Alfarol (registered trademark)), maxacalcitol (trade name: Oxarol (registered trademark)), tacalcitol (trade name: Bonalfa (registered trademark)), calcipotriol (trade name: Dovonex (registered trademark)), falecalcitriol (trade name: Hornel (registered trademark); trade name: Fulstan (registered trademark)), 2β-(3-hydroxypropyloxy)-1α,25-dihydroxyvitamin $D_3$ (ED-71(codename), Chugai Pharmaceutical Co., Ltd.) etc., are commercially available or under clinical development as vitamin D compounds (VD compounds) provided as drugs. Since a VD compound exhibits its pharmaceutical effects only in a trace amount and also exerts a hypercalcemic action as a side effect, its measurement with a high sensitivity is required. In recent years, with remarkable advances in mass spectrometry and liquid chromatography/mass spectrometry (LC/MS) as well as tandem liquid chromatography/mass spectrometry/mass spectrometry (LC/MS/MS) have been widely used for high sensitivity analysis of drugs and drug metabolite studies. Among others, electrospray ionization (ESI) and atmospheric pressure chemical ionization (APCI) are most frequently used. For VD compounds, LC/MS is often used as well. VD compounds like maxacalcitol, ED-71, etc., having hetero atoms such as an ester bond, ether bond, thioether bond, amide bond, etc. in their molecules, can be measured with a high sensitivity, whereas in VD compounds like alfacalcidol, cholecalciferol ($VD_3$), etc. having no hetero atoms such as an ester bond, ether bond, thioether bond, amide bond, etc. in the molecules, only about 1/5 to 1/100 sensitivity is achieved as compared to VD compounds having hetero atoms therein. It has thus been desired to develop a high sensitivity measurement method applicable to all VD compounds.

To achieve high sensitivity measurement of a VD compound by mass spectrometry, it is considered that derivatization is useful. For derivatization of a VD compound, triazoline derivatives (Cookson-type reagents), which selectively react with the triene structure in the Diels-Alder reaction, are frequently used [(1) Analytical Biochemistry 1992; 194: 77–81, (2) YAKUGAKU ZASSHI (Journal of the Pharmaceutical Society of Japan) 1998; 118(6): 206–215, (3) YAKUGAKU ZASSHI (Journal of the Pharmaceutical Society of Japan) 1999; 119(12): 898–920, (4) Biological Mass Spectrometry 1993; 22: 621–632, (5) Journal of Chromatography 1993; 645: 115–123, (6) Analytical Biochemistry 1996; 243: 28–40, etc.], and include PTAD (4-phenyl-1,2,4-triazoline-3,5-dione) [(4), (5) supra], PFBTAD (4-pentafluorobenzyl-1,2,4-triazoline-3,5-dione) [(5) supra], etc., utilizing resonance electron capture in LC/MS. It is reported that postcolumn derivatization of PTAD increases the sensitivity by 7 to 70 times but any case of applying PTAD to biological samples is unknown [(4) supra]. PFBTAD achieves 25 pg/mL (human plasma 1 mL), which is the lower limit of quantification [(6) supra] but this sensitivity is insufficient. According to our investigations, the sensitivity of only about 5 times was attained by derivatization in the technique utilizing PFPTAD (4-pentafluorophenyl-1,2,4-triazoline-3,5-dione) analogous to PFBTAD, and when applied to biological samples, sufficient sensitivity was not achieved because of a poor derivatization rate, etc. Therefore, it has been desired to develop reagents (derivatization agents) having atomic groups responsive to LC/MS with a high sensitivity.

Berkel et al. reported that ferrocene compounds are responsive with a high sensitivity and enable high sensitivity measurement when ferrocenyl azide is used as a derivatization agent for hydroxy group-containing compounds [(7) Analytical Chemistry 1998; 70: 1544–1554]. In ESI, ionic compounds can be measured with a high sensitivity and this derivatization technique takes advantage that ferrocene is readily oxidized upon ionization (positive ion mode) to produce stable ions efficiently. However, there is no report on the case in which this technique is applied to a method of measuring a VD compound. Moreover, when ferrocenyl azide is used as a derivatization agent, the technique encounters problems of difficult handling, since not only the reaction conditions require heating but also ferrocenyl azide itself is explosive.

As stated above, a method of measuring a vitamin D compound with a high sensitivity, which method is applicable to all kinds of the vitamin D compound and readily utilizable, a derivatization agent used for the method, and a combined compound of the derivatization agent and a vitamin D compound, are not available at the moment.

SUMMARY OF THE INVENTION

In order to solve these problems, the present inventors have made extensive investigations and found that, by combining a ferrocene compound represented by formula (1) below:

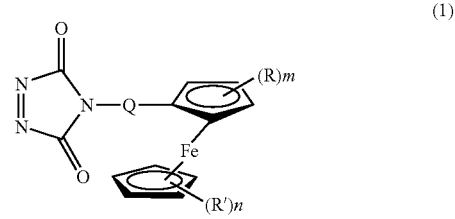

wherein Q represents a direct bond, alkylene or —$W_1$—X—$W_2$— (wherein $W_1$ represents an alkylene or phenylene; $W_2$ represents alkylene; X represents —O—, —N($R_a$)C(=O)—, —N($R_a$)C(=O)NH—, —OC(=O)NH— or —N($R_a$)OS(=O)—; and $R_a$ represents a lower alkyl group);

each of R and R' independently represents a hydrogen atom, hydroxy group, nitro group, cyano group, halogen, optionally substituted lower alkyl group, optionally substituted lower alkenyl group, optionally substituted lower alkynyl group, optionally substituted lower alkoxy group, optionally substituted lower acyl group, optionally substituted carboxy group, or optionally substituted carbamoyl group; m represents an integer of 1 to 3; and n represents an integer of 1 to 4, with a vitamin D compound (VD compound), and measuring the obtained compound by liquid chromatography/mass spectrometry (LC/MS), especially liquid chromatography/electrospray ionization-mass spectrometry/mass spectrometry (LC/ESI-MS/MS), the VD compound can be measured in a manner applicable to all VD compounds and readily available and further with a higher sensitivity than never before. The present invention has thus been accomplished.

That is, the present invention relates to a ferrocene compound represented by formula (1) described below.

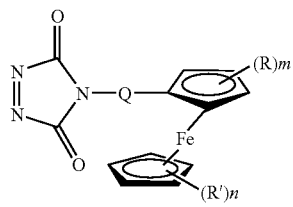

(1)

wherein Q represents a direct bond, alkylene or —$W_1$—X—$W_2$— (wherein $W_1$ represents alkylene or phenylene; $W_2$ represents alkylene; X represents —O—, —N($R_a$)C(=O)—, —N($R_a$)C(=O)NH—, —OC(=O)NH— or —N($R_a$)OS(=O)—; and $R_a$ represents a lower alkyl group); each of R and R' independently represents a hydrogen atom, hydroxy group, nitro group, cyano group, halogen, optionally substituted lower alkyl group, optionally substituted lower alkenyl group, optionally substituted lower alkynyl group, optionally substituted lower alkoxy group, optionally substituted lower acyl group, optionally substituted carboxy group, or optionally substituted carbamoyl group; m represents an integer of 1 to 3; and n represents an integer of 1 to 4.

In the compound represented by the formula (1) described above, the present invention further relates to the ferrocene compound wherein R and R' are hydrogen atoms. In the compound represented by the formula (1) described above, the present invention further relates to the ferrocene compound wherein Q represents a direct bond or alkylene. The present invention further relates to the ferrocene compound wherein Q is methylene and the ferrocene compound wherein Q is a direct bond.

Specific examples of the ferrocene compound of the present invention are 4-(ferrocenylmethyl)-1,2,4-triazoline-3,5-dione (FMTAD), 4-ferrocenyl-1,2,4-triazoline-3,5-dione (FTAD), and the like.

Furthermore, the present invention relates to a reagent comprising the ferrocene compound described above for measuring a compound having a triene structure. Such a reagent can further contain a solvent which is capable of dissolving the ferrocene compound.

The present invention further relates to a combined compound of a ferrocene compound represented by formula (1) described below, and a vitamin D compound:

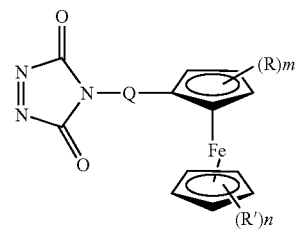

(1)

wherein Q represents a direct bond, alkylene or —$W_1$—X—$W_2$— (wherein $W_1$ represents alkylene or phenylene; $W_2$ represents alkylene; X represents —O—, —N($R_a$)C(=O)—, —N($R_a$)C(=O)NH—, —OC(=O)NH— or —N($R_a$)OS(=O)—; and $R_a$ represents a lower alkyl group); each of R and R' independently represents a hydrogen atom, hydroxy group, nitro group, cyano group, halogen, optionally substituted lower alkyl group, optionally substituted lower alkenyl group, optionally substituted lower alkynyl group, optionally substituted lower alkoxy group, optionally substituted lower acyl group, optionally substituted carboxy group, or optionally substituted carbamoyl group; m represents an integer of 1 to 3; and n represents an integer of 1 to 4.

In the compound described above, the present invention further relates to the combined compound of a ferrocene compound and a vitamin D compound, wherein the ferrocene compound and the vitamin D compound have been combined with each other through a covalent bond.

The present invention still further relates to a combined compound of a ferrocene compound and a vitamin D compound, wherein the combined compound of the ferrocene compound and a vitamin D compound is represented by formula (2) below:

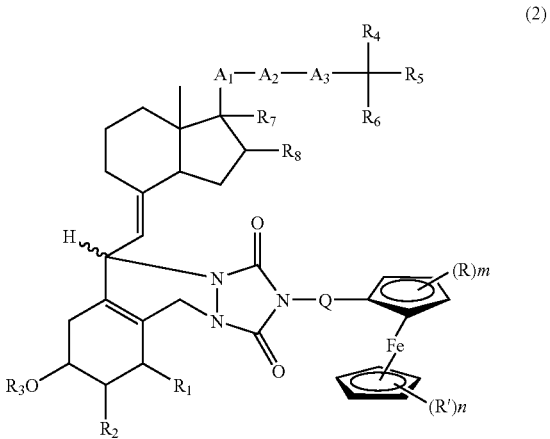

(2)

wherein each of $A_1$ and $A_3$ independently represents optionally substituted lower alkylene, optionally substituted lower alkenylene, or optionally substituted lower alkynylene; $A_2$ represents a direct bond, —CH=CH—, —C≡C—, —O—, —S— or —NH—; $R_1$ represents a hydrogen atom or —$OR_9$ ($R_9$ represents a hydrogen atom or a protecting group); $R_2$ represents a hydrogen atom, hydroxy group, halogen, optionally substituted lower alkyl group, optionally substituted lower alkenyl group, optionally substituted lower alkynyl group, optionally substituted lower alkoxy group or optionally substituted lower acyl group; R₃ represents a hydrogen atom or protecting group; each of R₄, R₅ and R₆ independently represents a hydrogen atom, hydroxy group, nitro group, cyano group, halogen, optionally substituted lower alkyl group, optionally substituted cycloalkyl group, optionally substituted lower alkenyl group, optionally substituted lower alkynyl group, optionally substituted lower alkoxy group, optionally substituted lower acyl group, optionally substituted carboxy group, optionally substituted carbamoyl group or optionally substituted amino group; each of R₇ and R₈ independently represents a hydrogen atom or hydroxy group, or, R₇ and R₈ are linked together to form a double bond; Q represents a direct bond, alkylene or —W₁—X—W₂— (wherein W₁ represents alkylene or phenylene; W₂ represents alkylene; X represents —O—, —N(Rₐ)C(=O)—, —N(Rₐ)C(=O)NH—, —OC(=O)NH— or —N(Rₐ)OS(=O)—, and Rₐ represents a lower alkyl group); each of R and R' independently represents a hydrogen atom, hydroxy group, nitro group, cyano group, halogen, optionally substituted lower alkyl group, optionally substituted lower alkenyl group, optionally substituted lower alkynyl group, optionally substituted lower alkoxy group, optionally substituted lower acyl group, optionally substituted carboxy group or optionally substituted carbamoyl group; m represents an integer of 1 to 3; and n represents an integer of 1 to 4.).

In the compound represented by formula (2) described above, the present invention further relates to the compound, wherein A₁-A₂-A₃ represents —CH(CH₃)—(CH₂)₃—, —CH(CH₃)—CH=CH— or —CH(CH₃)—CH=CH—CH=CH—; R₁ represents a hydrogen atom or hydroxy group; R₂ represents a hydrogen atom or hydroxypropoxy group; R₃ represents a hydrogen atom; each of R₄, R₅ and R₆ independently represents a hydrogen atom, hydroxy group, lower alkyl group which may optionally be substituted with halogen, or lower cycloalkyl group which may optionally be substituted with a halogen; R₇ and R₈ represent a hydrogen atom, or, R₇ and R₈ are linked together to form a double bond. In the compound represented by formula (2) described above, the present invention further relates to the compound, wherein R and R' are a hydrogen atom.

In the compound represented by formula (2) described above, the present invention further relates to the combined compound of the ferrocene compound and a vitamin D compound, wherein Q represents a direct bond or alkylene. Still further, the present invention relates to the combined compound of the ferrocene compound and a vitamin D compound, wherein Q is methylene, and the combined compound of the ferrocene compound and a vitamin D compound, wherein Q is a direct bond. In the combined compound of the ferrocene compound and a vitamin D compound, the present invention still further relates to the combined compound of the ferrocene compound and a vitamin D compound, wherein the vitamin D compound is vitamin D₃ compound.

The present invention still further relates to a method of measuring a vitamin D compound contained in a sample, which comprises reacting a ferrocene compound represented by formula (1) below:

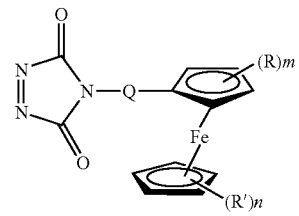

wherein Q represents a direct bond, alkylene or —W₁—X—W₂— (wherein W₁ represents alkylene or phenylene; W₂ represents alkylene; X represents —O—, —N(Rₐ)C(=O)—, —N(Rₐ)C(=O)NH—, —OC(=O)NH— or —N(Rₐ)OS(=O)—; and Rₐ represents a lower alkyl group); each of R and R' independently represents a hydrogen atom, hydroxy group, nitro group, cyano group, halogen, optionally substituted lower alkyl group, optionally substituted lower alkenyl group, optionally substituted lower alkynyl group, optionally substituted lower alkoxy group, optionally substituted lower acyl group, optionally substituted carboxy group, or optionally substituted carbamoyl group; m represents an integer of 1 to 3; and n represents an integer of 1 to 4, with the vitamin D compound in a sample, and measuring the resulting combined compound of the ferrocene compound and the vitamin D compound, which have been combined with each other, by liquid chromatography/mass spectrometry (LC/MS).

The present invention further relates to the method of measuring a vitamin D compound, wherein the combined compound of the ferrocene compound and a vitamin D compound is a compound wherein the ferrocene compound and the vitamin D compound have been combined with each other through a covalent bond.

The present invention still further relates to the method of measuring a vitamin D compound, wherein the combined compound of the ferrocene compound and the vitamin D compound is represented by formula (2) below:

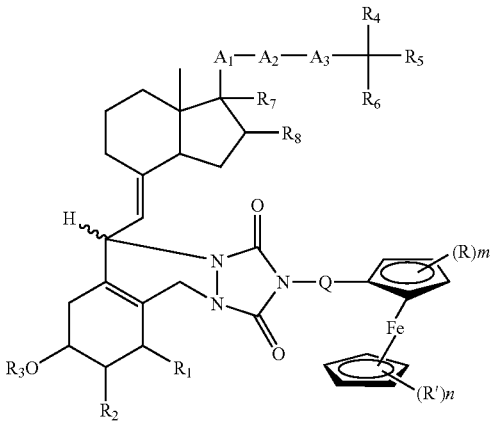

wherein each of A₁ and A₃ independently represents optionally substituted lower alkylene, optionally substituted lower alkenylene, or optionally substituted lower alkynylene; A₂ represents a direct bond, —CH=CH—, —C≡C—, —O—, —S— or —NH—; $R_1$ represents a hydrogen atom or —$OR_9$ ($R_9$ represents hydrogen atom or a protecting group); $R_2$ represents a hydrogen atom, hydroxy group, halogen, optionally substituted lower alkyl group, optionally substituted lower alkenyl group, optionally substituted lower alkynyl group, optionally substituted lower alkoxy group or optionally substituted lower acyl group; $R_3$ represents a hydrogen atom or protecting group; each of $R_4$, $R_5$ and $R_6$ independently represents a hydrogen atom, hydroxy group, nitro group, cyano group, halogen, optionally substituted lower alkyl group, optionally substituted cycloalkyl group, optionally substituted lower alkenyl group, optionally substituted lower alkynyl group, optionally substituted lower alkoxy group, optionally substituted lower acyl group, optionally substituted carboxy group, optionally substituted carbamoyl group or optionally substituted amino group; each of $R_7$ and $R_8$ independently represents a hydrogen atom or hydroxy group, or, $R_7$ and $R_8$ are linked together to form a double bond; Q represents a direct bond, alkylene or —$W_1$—X—$W_2$— (wherein $W_1$ represents alkylene or phenylene; $W_2$ represents alkylene; X represents —O—, —N($R_a$)C(=O)—, —N($R_a$)C(=O)NH—, —OC(=O)NH— or —N($R_a$)OS(=O)—, and $R_a$ represents a lower alkyl group); each of R and R' independently represents a hydrogen atom, hydroxy group, nitro group, cyano group, halogen, optionally substituted lower alkyl group, optionally substituted lower alkenyl group, optionally substituted lower alkynyl group, optionally substituted lower alkoxy group, optionally substituted lower acyl group, optionally substituted carboxy group or optionally substituted carbamoyl group; m represents an integer of 1 to 3; and n represents an integer of 1 to 4.

The present invention still further relates to the method of measuring a vitamin D compound, wherein, in the compound described above and the combined compound of the ferrocene compound and a vitamin D compound described above, $A_1$-$A_2$-$A_3$ represents —CH($CH_3$)—($CH_2$)$_3$—, —CH($CH_3$)—CH=CH— or —CH($CH_3$)—CH=CH—CH=CH—; $R_1$ represents a hydrogen atom or hydroxy group; $R_2$ represents a hydrogen atom or hydroxypropoxy group; $R_3$ represents a hydrogen atom; each of $R_4$, $R_5$ and $R_6$ independently represents a hydrogen atom, hydroxy group, lower alkyl group which may optionally be substituted with halogen, or a lower cycloalkyl group which may optionally be substituted with halogen; $R_7$ and $R_8$ represent a hydrogen atom, or, $R_7$ and $R_8$ are linked together to form a double bond. The present invention still further relates to the method of measuring a vitamin D compound, wherein R and R' are a hydrogen atom in the compound described above and the combined compound of the ferrocene compound and a vitamin D compound described above. The present invention still further relates to the method of measuring a vitamin D compound, wherein the combined compound of the ferrocene compound and a vitamin D compound is a combined compound of the ferrocene compound and a VD compound among the compounds represented by the formula above, wherein Q represents a direct bond or alkylene. The present invention still further relates to the method of measuring a vitamin D compound, wherein the combined compound is a combined compound of the ferrocene compound and a vitamin D compound, wherein Q is methylene; and the method of measuring a vitamin D compound, wherein the combined compound is a combined compound of the ferrocene compound and a vitamin D compound, wherein Q is a direct bond.

The present invention still further relates to the method of measuring a vitamin D compound, wherein the combined compound is a combined compound of the ferrocene compound and a vitamin D compound in which the vitamin D compound is a vitamin $D_3$ compound.

The present invention still further relates to the method of measuring a vitamin D compound, wherein the sample (analyte sample) is a sample taken from a living body.

The present invention still further relates to the method of measuring a vitamin D compound, wherein the liquid chromatography/mass spectrometry (LC/MS) is liquid chromatography/electrospray ionization-mass spectrometry/mass spectrometry (LC/ESI-MS/MS).

DETAILED DESCRIPTION OF THE INVENTION

Figure 1:
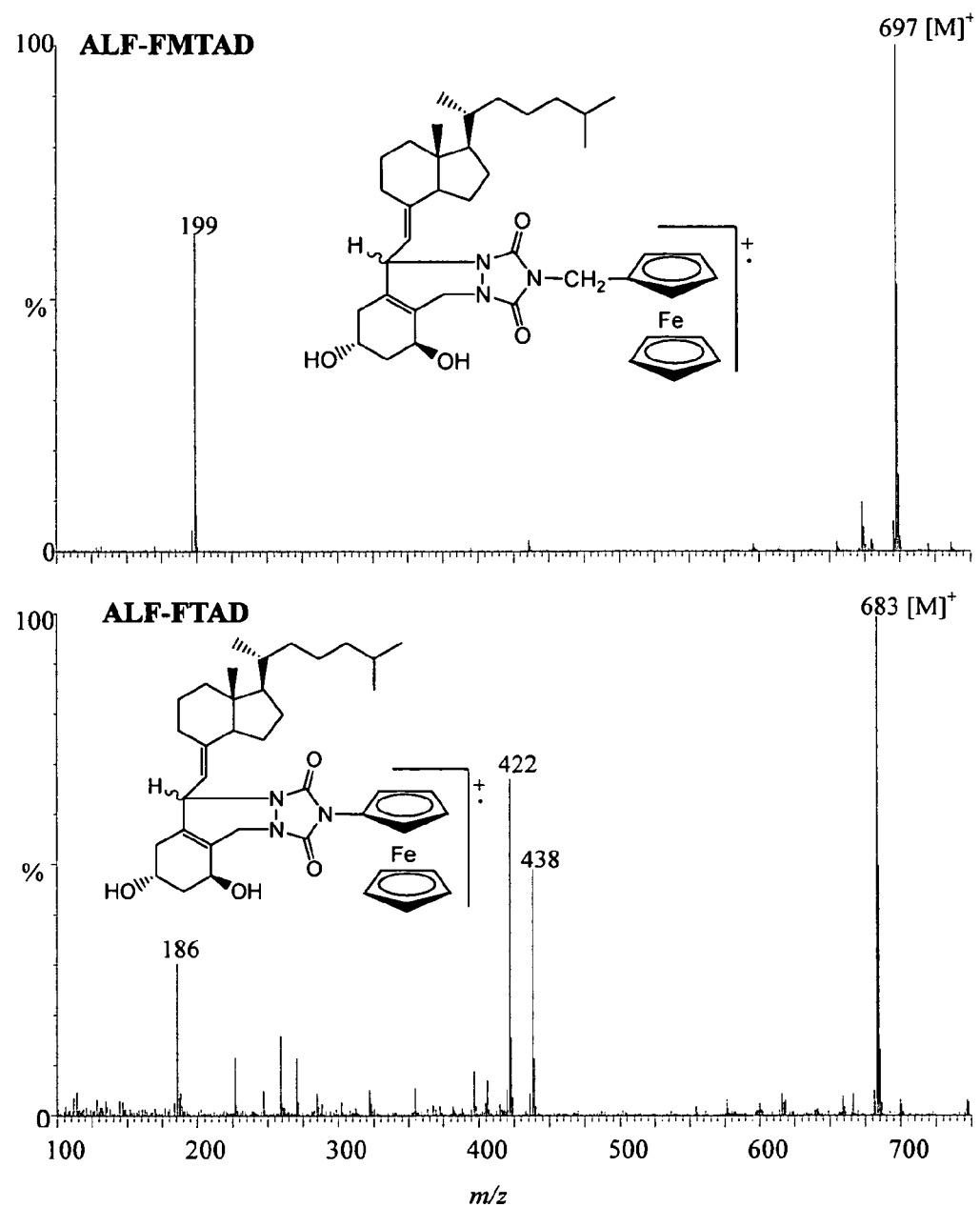
FIG. 1 illustrates an example of the results when the ESI mass spectra of ALF-FMTAD and ALF-FTAD were measured.

Hereinafter, the present invention will be described more specifically.

In the ferrocene compound represented by formula (1) below:

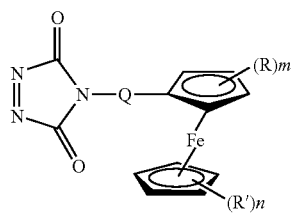
(1)

"Q" represents a direct bond, alkylene or —$W_1$—X—$W_2$— (wherein $W_1$ represents alkylene or phenylene; $W_2$ represents alkylene; X represents —O—, —N($R_a$)C(=O)—, —N($R_a$)C(=O)NH—, —OC(=O)NH— or —N($R_a$)OS(=O)—, and $R_a$ represents a lower alkyl group), preferably represents a direct bond, alkylene or —$W_1$—X—$W_2$— (wherein $W_1$ represents methylene or phenylene; $W_2$ represents methylene; X represents —O—, —N(CH$_3$)C(=O)—, —N(CH$_3$)C(=O)NH— or —OC(=O)NH—); more preferably, Q represents a direct bond or an alkylene, much more preferably, alkylene, and most preferably, methylene. In "$R_a$", the "lower alkyl group" means a straight or branched alkyl group having 1 to 6 carbon atoms such as methyl, ethyl, propyl, isopropyl, butyl, isobutyl, s-butyl, t-butyl, pentyl, isopentyl, neopentyl, hexyl, etc.

The "alkylene" in Q, "$W_1$ and $W_2$" described above means a straight or branched alkylene chain having 1 to 6 carbon atoms such as methylene, ethylene, propylene, isopropylene, butylenes, etc. The "phenylene" in $W_1$ means o-phenylene, m-phenylene or p-phenylene.

Each of "R" and "R'" described above independently represents hydrogen atom, hydroxy group, nitro group, cyano group, halogen, optionally substituted lower alkyl group, optionally substituted lower alkenyl group, optionally substituted lower alkynyl group, optionally substituted lower alkoxy group, optionally substituted lower acyl group, optionally substituted carboxy group or optionally substituted carbamoyl group; preferably, hydrogen atom, hydroxy group, halogen or lower alkyl group, and more preferably, hydrogen atom. Herein, the "halogen" means chlorine, fluorine, bromine, iodine, etc.; the "lower alkyl group" means a straight or branched alkyl group having 1 to 6 carbon atoms such as methyl, ethyl, propyl, isopropyl, butyl, isobutyl, s-butyl, t-butyl, pentyl, isopentyl, neopentyl, hexyl, etc.; the "lower alkenyl group" means a straight or branched alkenyl group having 1 to 6 carbon atoms, such as ethenyl, 1-propenyl, allyl, 1-butenyl, 2-butenyl, 3-butenyl, pentenyl, hexenyl, etc.; the "lower alkynyl group" means a straight or branched alkynyl group having 1 to 6 carbon atoms, such as ethynyl, propynyl, butynyl, pentynyl, hexynyl, etc.; the "lower alkoxy group" means an alkoxy group having 1 to 6 carbon atoms, such as methoxy, ethoxy, propoxy, isopropoxy, butoxy, pentyloxy, hexyloxy, phenoxy, etc.; and the "lower acyl group" means an acyl group having 1 to 6 carbon atoms, such as formyl, acetyl, propionyl, butyryl, isobutyryl, valeryl, isovaleryl, pivaloyl, hexanoyl, etc.

In the substituent(s) described above, "optionally substituted" means that these groups may optionally have 1 or more (e.g., 1 to 3) substituents, including hydroxy group; nitro group; cyano group; halogen such as chlorine, fluorine, bromine, iodine, etc.; a straight or branched alkyl group having 1 to 6 carbon atoms such as methyl, ethyl, propyl, isopropyl, butyl, isobutyl, s-butyl, t-butyl, pentyl, isopentyl, neopentyl, hexyl, etc.; a straight or branched alkenyl group having 1 to 6 carbon atoms, such as ethenyl, 1-propenyl, allyl, 1-butenyl, 2-butenyl, 3-butenyl, pentenyl, hexenyl, etc.; a straight or branched alkynyl group having 1 to 6 carbon atoms, such as ethynyl, propynyl, butynyl, pentynyl, hexynyl, etc.; an alkoxy group having 1 to 6 carbon atoms, such as methoxy, ethoxy, propoxy, isopropoxy, butoxy, pentyloxy, hexyloxy, phenoxy, etc.; an acyl group having 1 to 6 carbon atoms, such as formyl, acetyl, propionyl, butyryl, isobutyryl, valeryl, isovaleryl, pivaloyl, hexanoyl, etc.; carboxy group; carbamoyl group; and/or amino group, etc.

The ferrocene compound of the present invention (Compound 6 in the production scheme described below) can be produced in accordance with the production scheme below:

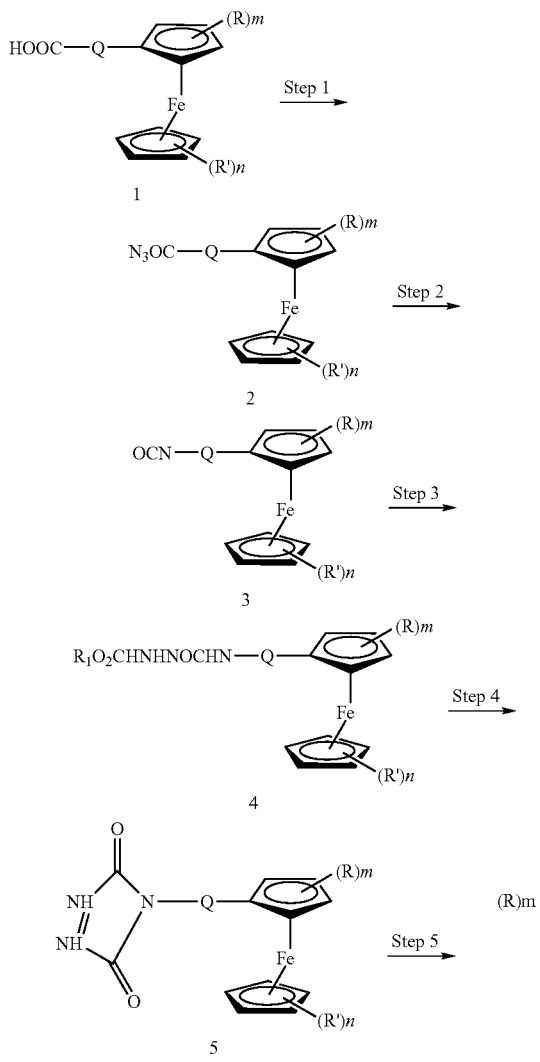

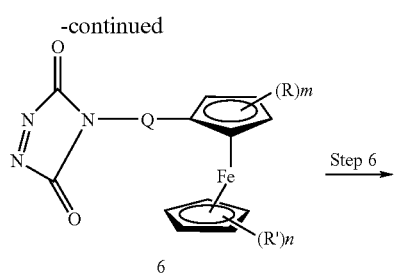

(wherein Q, R, R', m and n have the same significance as defined in formula (1) described above).

In Step 1, Compound 2 can be synthesized from Compound 1 by a process which involves reacting with diphenylphosphorylazide and a base, a process which involves converting the carboxylic acid into the acid chloride or acid anhydride followed by reacting with sodium azide, a process which involves converting the carboxylic acid into the ester, reacting with hydrazine, converting into the amide with hydrazine and then reacting with nitric acid or a nitric acid ester, etc.; preferably by the process which involves reacting with diphenylphosphorylazide and a base. Compound 1, which is the starting material, is known or can be readily synthesized from known compounds by known synthesis techniques. In addition, Compound 1 is commercially available and can be purchased from, e.g., Tokyo Kasei Kogyo Co., Ltd. In the process of reacting with diphenylphosphorylazide and a base, examples of the base used are triethylamine, diisopropylethylamine, etc., preferably triethylamine. In the process of reacting with diphenylphosphorylazide and a base, examples of solvents used are dichloromethane, chloroform, dichloroethane, benzene, toluene, xylene, tetrahydrofuran, diethyl ether, dioxane, dimethoxyethane, etc., preferably dichloromethane. In the process of reacting with diphenylphosphorylazide and a base, the reaction temperature is not particularly limited so long as it is a temperature at which the reaction proceeds, but the reaction is carried out generally at $-78$ to $50°$ C., preferably at $-10$ to $10°$ C.

In Step 2, Compound 3 can be synthesized by heating Compound 2. Examples of solvents used in Step 2 described above are dichloromethane, chloroform, dichloroethane, benzene, toluene, xylene, tetrahydrofuran, diethyl ether, dioxane, dimethoxyethane, etc., preferably toluene. Though reaction temperature is not particularly limited so long as it is a temperature at which the reaction proceeds, the reaction is carried out generally at $20$ to $200°$ C., preferably at $50$ to $150°$ C.

In Step 3, Compound 4 can be produced by reacting Compound 3 with a carbazinic acid ester. Examples of solvents used in Step 3 described above are dichloromethane, chloroform, dichloroethane, benzene, toluene, xylene, tetrahydrofuran, diethyl ether, dioxane, dimethoxyethane, etc., preferably toluene. While the reaction temperature is not particularly limited so long as it is a temperature at which the reaction proceeds, the reaction is carried out generally at $0$ to $200°$ C., preferably at $20$ to $120°$ C.

In Step 4, Compound 5 can be produced by reacting Compound 4 with a base. Examples of the base used in Step 4 described above include sodium methoxide, sodium ethoxide, sodium tert-butoxylate, potassium methoxide, potassium ethoxide, potassium tert-butoxide, n-butyl lithium, sec-butyl lithium, tert-butyl lithium, lithium diisopropylamide, lithium dicyclohexylamide, lithium bis(trimethylsilyl)amide, potassium bis(trimethylsilyl)amide, sodium hydride, potassium hydride, sodium hydrogencarbonate, potassium hydrogencarbonate, potassium carbonate, sodium carbonate, calcium carbonate, cesium carbonate, etc., preferably potassium carbonate. Examples of solvents used in Step 4 described above are methanol, ethanol, isopropanol, dichloromethane, chloroform, dichloroethane, benzene, toluene, xylene, tetrahydrofuran, diethyl ether, dioxane, dimethoxyethane, etc., preferably ethanol. Although the reaction temperature is not particularly limited so long as it is a temperature at which the reaction proceeds, the reaction is carried out generally at $0$ to $200°$ C., preferably at $20$ to $120°$ C.

In Step 5, Compound 6 can be produced by reacting Compound 5 with iodobenzene diacetate. Examples of solvents used in Step 4 described above are ethyl acetate, dichloromethane, chloroform, dichloroethane, benzene, toluene, xylene, tetrahydrofuran (THF), diethyl ether, dioxane, dimethoxyethane, etc., preferably tetrahydrofuran (THF) or dioxane. Though the reaction temperature is not particularly limited so long as it is a temperature at which the reaction proceeds, the reaction is carried out generally at $-78$ to $100°$ C., preferably at $-10$ to $50°$ C.

In addition, the ferrocene compound of the present invention (in Compound 6, the compound wherein Q is $W_1$—X—$W_2$) can also be produced in accordance with the production scheme described below:

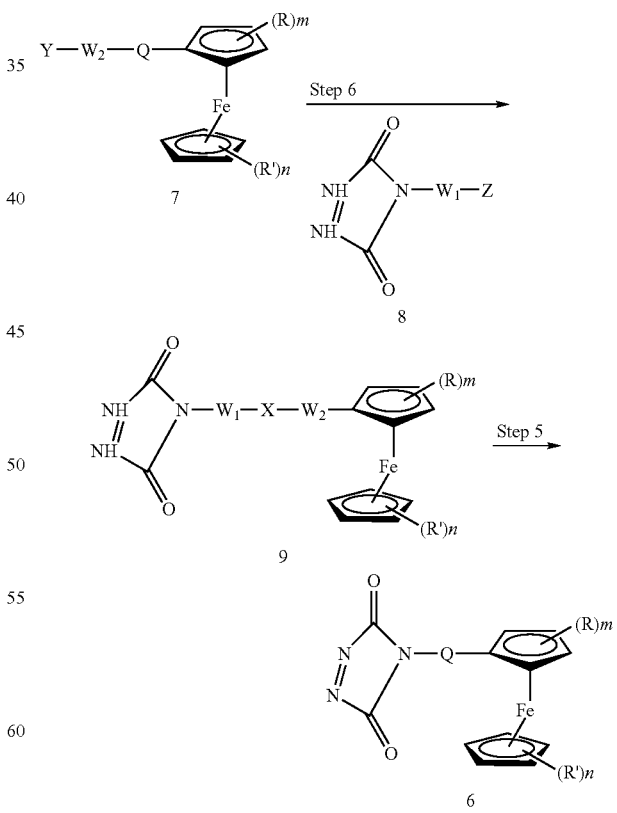

(wherein Q, R, R', $W_1$, X, $W_2$, m and n have the same significance as defined in formula (1) described above).

In Step 6, Compound 9 can also be synthesized by reacting Compound 7 (Y represents a hydroxy group, carboxylic acid chloride residue, carboxylic acid anhydride residue, carboxylic acid ester group, isocyanate group, sulfonyl chloride residue, halogen atom, alkylsulfonyloxy group or arylsulfonyloxy group) with Compound 8 (Z represents a hydroxy group, optionally substituted amino group, halogen atom, alkylsulfonyloxy group or arylsulfonyloxy group) (Step 6). In this case, the reaction is carried out preferably in the presence of a base. For the combination of Y and Z, there are the combination of Compound 7 wherein Y is a carboxylic acid chloride residue, carboxylic acid anhydride residue, carboxylic acid ester group, isocyanate group or sulfonyl chloride residue and Compound 8 wherein Z is a hydroxy group or optionally substituted amino group; the combination of Compound 7 wherein Y is a hydroxy group and Compound 8 wherein Z is a halogen atom, alkylsulfonyloxy group or arylsulfonyloxy group; or the combination of Compound 7 wherein Y is a halogen atom, alkylsulfonyloxy group or arylsulfonyloxy group and Compound 8 wherein Z is a hydroxy group. Compound 7 and Compound 8, which are the starting materials, are known or can readily be synthesized from known compounds by known processes. Compound 7 is also commercially available and can be purchased from Tokyo Kasei Kogyo Co., Ltd. Examples of the base used in Step 6 described above include sodium hydroxide, potassium hydroxide, sodium hydrogencarbonate, potassium hydrogencarbonate, sodium hydride, potassium hydride, potassium carbonate, sodium carbonate, calcium carbonate, cesium carbonate, triethylamine, diisopropylethylamine, pyridine, 2,6-dimethylpyridine, 2,4,6-trimethylpyridine, 4-(dimethylamino)pyridine, etc. Examples of solvents used in Step 6 described above include water, methanol, ethanol, isopropanol, dichloromethane, chloroform, dichloroethane, benzene, toluene, xylene, tetrahydrofuran, diethyl ether, dioxane, dimethoxyethane, etc. While the reaction temperature is not particularly limited so long as it is a temperature at which the reaction proceeds, the reaction is carried out generally at −78 to 200° C., preferably at −10 to 150° C.

The ferrocene compound of the present invention thus obtained can be isolated, if necessary, by applying operations like purification, drying, etc. in accordance with known techniques. The ferrocene compound obtained may be sometimes unstable and in such a case, can be stored in a solvent in which the compound can be stably present (e.g., tetrahydrofuran, dioxane, etc.).

The ferrocene compound of the present invention is useful as a reagent (derivatization agent) when compounds having a triene structure, e.g., vitamin D compounds (VD compounds), etc. are measured by liquid chromatography/mass spectrometry (LC/MS), especially liquid chromatography/electrospray ionization-mass spectrometry/mass spectrometry (LC/ESI-MS/MS).

The reagent of the present invention means both the aforesaid ferrocene compound itself and a solution containing the ferrocene compound described above. Examples of solvents which can be used for the reagent of the present invention include ethyl acetate, dichloromethane, chloroform, dichloroethane, benzene, toluene, xylene, tetrahydrofuran (THF), diethyl ether, dioxane, dimethoxyethane, etc., preferably tetrahydrofuran (THF) or dioxane. While the content of the ferrocene compound in the solution is not particularly limited, it is appropriately chosen from the range of, e.g., 0.001 to 99% by weight, preferably 0.005 to 50% by weight, and more preferably 0.01 to 10% by weight. Where a target compound is measured using the reagent of the present invention, specifically the ferrocene compound in the reagent is reacted with a VD compound, and the resulting compound obtained by combining the ferrocene compound and the VD compound, is applied to LC/ESI-MS/MS, etc., thereby to measure the VD compound. Details of the measurement will be described later.

Herein, the VD compound, with which the ferrocene compound of the present invention is to be combined (namely, the VD compound as an analyte), is preferably a vitamin $D_3$ compound (a $VD_3$ compound). Herein, the $VD_3$ compound includes a compound having the 9,10-secocholesta-5,7,10(19)-triene structure, preferably a compound having the (5Z,7E)-9,10-secocholesta-5,7,10(19)-triene structure, more preferably, a compound having the (1α,5Z, 7E)-9,10-secocholesta-5,7,10(19)-trien-1-ol structure, a compound having the (3β,5Z,7E)-9,10-secocholesta-5,7,10 (19)-trien-3-ol structure, or a compound having the (1α,5Z, 7E)-9,10-secocholesta-5,7,10(19)-triene-1,3-diol structure. Specific examples of these $VD_3$ compounds are cholecalciferol ($VD_3$), calcitriol (1α,25(OH)$_2$D$_3$; trade name: Rocaltrol (registered trademark), capsule/manufactured and sold by Chugai Pharmaceutical Co., Ltd., sold by Kyorin Pharmaceutical Co., Ltd., note/import origin: Chugai Pharmaceutical Co., Ltd., sales destination: Kirin Brewery Co., Ltd.), alfacalcidol (ALF; trade name: Alfarol (registered trademark), Chugai Pharmaceutical Co., Ltd.; Japanese Patent Publication (KOKAI) No. 48-62750 and Tetrahedron Lett., 1973, 2339, Tetrahedron, 30, 2701(1974), etc.), maxacalcitol (OCT; trade name: Oxarol (registered trademark), ointment/sales destination: Maruho Co., Ltd., manufactured by Chugai Seiyaku Co., Ltd. Chugai Pharmaceutical Co., Ltd., note/manufactured and sold by Chugai Pharmaceutical Co., Ltd.; Japanese Patent Publication (KOKAI) No. 61-267550, etc.), tacalcitol (trade name: Bonalfa (registered trademark), Teijin Ltd.), calcipotriol (trade name: Dovonex (registered trademark), imported by Teikoku Seiyaku Co., Ltd., sold by Fujisawa Pharmaceutical Co., Ltd., Teikoku Medix Co., Ltd.), falecalcitriol (trade name: Hornel (registered trademark), Taisho Pharmaceutical Co., Ltd.; trade name: Fulstan (registered trademark), manufactured by Sumitomo Pharmaceuticals Co., Ltd., sold by Kissei Pharmaceutical Co., Ltd.), 2β-(3-hydroxypropyloxy)-1α,25-dihydroxyvitamin $D_3$ (ED-71 (code name), Chugai Pharmaceutical Co., Ltd.; Japanese Patent Publication (KOKAI) No. 61-267548, etc.), EB1089 (code name, Leo Pharmaceutical Products, Inc.; J. Chromatogr. B, 740, 117–128 (2000), etc.), compounds described in International Publications WO 95/27697, WO 98/28266, WO 00/49403, WO 00/61776, WO 00/64870, WO 00/66548, WO 01/16099, WO 01/62723, WO 01/79166, WO 01/90061, WO 01/96293, WO 02/13832, etc. Herein, $VD_3$, 1α,25(OH)$_2$D$_3$, ALF, etc. are commercially available and can be purchased from, e.g., Solvay Pharmaceutical, Inc., CALBIO, Inc., FLUKA Inc., FORMOSA Corp., WAKO, etc. Typical structures of these compounds are shown below.

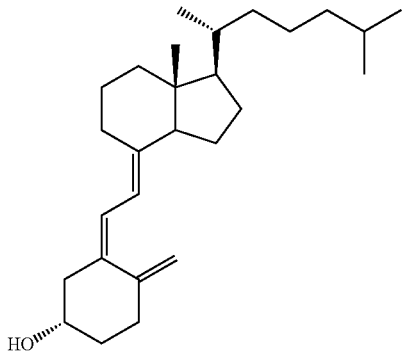

• Cholecalciferol (VD₃)

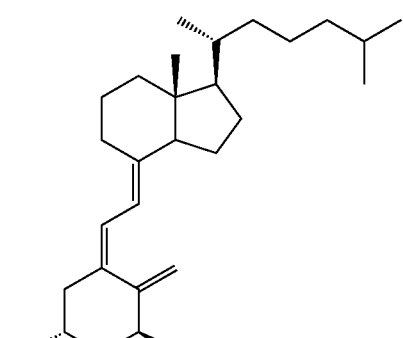

• Alfacalcidol (ALF)

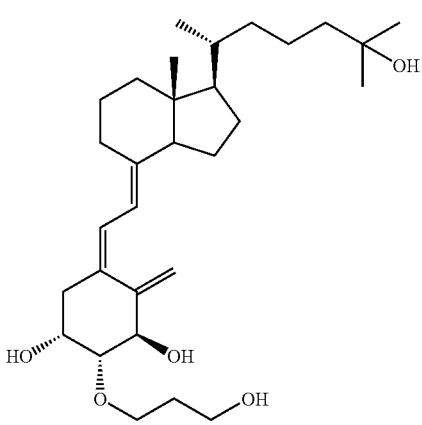

• 2β-(3-Hydroxypropyloxy)-1α, 25-dihydroxyvitamin D₃ (ED-71)

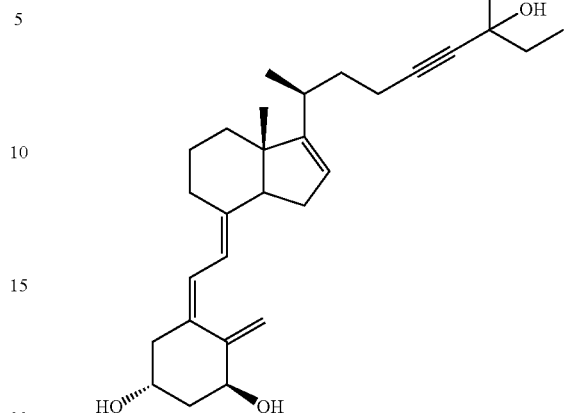

• Compound described in International Publication WO 02/13832, EXAMPLE 6 (hereinafter referred to as Compound A)

In VD compounds (i.e., VD compounds as analytes) which are to be combined with the ferrocene compounds of the present invention described above, particularly preferred are VD compounds having no hetero atom such as an ester bond, ether bond, thioether bond, amide bond, etc., in the molecule (specifically VD₃, calcipotriol, 1α,25(OH)₂D₃, ALF, falecalcitriol, EB1089 and Compound A described above, etc.).

To combine the ferrocene compound of the present invention with the VD compound, the triazone skeleton of the ferrocene compound of the present invention may be selectively reacted with the triene structure of the VD compound by the Diels-Alder reaction. Specifically, the ferrocene compound of the present invention is reacted with the VD compound for 5 minutes to 5 hours (preferably 15 minutes to 3 hours) in a suitable solvent such as ethyl acetate, dichloromethane, chloroform, dichloroethane, benzene, toluene, xylene, tetrahydrofuran (THF), diethyl ether, dioxane, dimethoxyethane (preferably tetrahydrofuran (THF) or dioxane), etc. Though the reaction temperature is not particularly limited so long as it is a temperature at which the reaction proceeds, the reaction is carried out generally at −78 to 100° C., preferably at −10 to 50° C. In order to terminate the reaction depending on necessity, water or an alcoholic solvent such as methanol, ethanol, propanol, isopropanol, etc. may be added. The compound thus obtained by combining the ferrocene compound and the VD compound, can be isolated, if necessary, by performing operations such as purification, drying, etc., following known methods.

The combined compound thus obtained, which comprises the ferrocene compound and the VD compound which have been combined with each other, is a compound in which the ferrocene compound and the VD compound have been combined with each other through a covalent bond.

Preferably, the combined compound of the ferrocene compound and the VD compound is represented by formula (2) below.

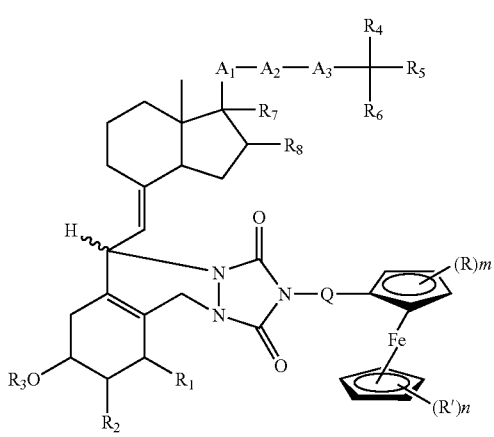

(2)

Herein, "Q, R, R', m and n" in the formula above have the same significance as defined in formula (1) described above. Each of "$A_1$ and $A_3$" independently represents optionally substituted lower alkylene, optionally substituted lower alkenylene or optionally substituted lower alkynylene. "$A_2$" represents a direct bond, —CH═CH—, —C≡C—, —O—, —S— or —NH—, preferably a direct bond, —CH═CH— or —C≡C—. Preferably, $A_1$-$A_2$-$A_3$ is —CH(CH$_3$)—(CH$_2$)$_3$—, —CH(CH$_3$)—CH═CH— or —CH(CH$_3$)—CH═CH—CH═CH—, and most preferably —CH(CH$_3$)—(CH$_2$)$_3$—. "$R_1$" represents a hydrogen atom or —OR$_9$ ($R_9$ represents a hydrogen atom or protecting group), preferably a hydrogen atom or hydroxy group. "$R_2$" represents a hydrogen atom, hydroxy group, halogen, optionally substituted lower alkyl group, optionally substituted lower alkenyl group, optionally substituted lower alkynyl group, optionally substituted lower alkoxy group or optionally substituted lower acyl group, preferably a hydrogen atom or hydroxypropoxy group. "$R_3$" represents a hydrogen atom or protecting group, preferably a hydrogen atom. Each of "$R_4$, $R_5$ and $R_6$" independently represents a hydrogen atom, hydroxy group, nitro group, cyano group, halogen, optionally substituted lower alkyl group, optionally substituted cycloalkyl group, optionally substituted lower alkenyl group, optionally substituted lower alkynyl group, optionally substituted lower alkoxy group, optionally substituted lower acyl group, optionally substituted carboxy group, optionally substituted carbamoyl group or optionally substituted amino group, preferably, each independently represents a hydrogen atom, hydroxy group, lower alkyl group which may optionally be substituted with a halogen, or lower cycloalkyl group which may optionally be substituted with a halogen. Each of "$R_7$ and $R_8$" independently represents a hydrogen atom or hydroxy group, or, $R_7$ and $R_8$ are linked together to form a double bond, preferably a hydrogen atom or $R_7$ and $R_8$ are linked together to form a double bond.

In $A_1$ and $A_3$ described above, the "lower alkylene" means a straight or branched alkylene chain having 1 to 6 carbon atoms, the "lower alkenylene" means a straight or branched alkenylene chain having 1 to 6 carbon atoms, and the "lower alkynylene" means a straight or branched alkynylene chain having 1 to 6 carbon atoms. The term "optionally substituted" means that these groups may optionally have 1 or more (e.g., 1 to 3) substituents, such as a hydroxy group; nitro group; cyano group; halogen such as chlorine, fluorine, bromine, iodine, etc.; straight or branched alkyl group having 1 to 6 carbon atoms such as methyl, ethyl, propyl, isopropyl, butyl, isobutyl, s-butyl, t-butyl, pentyl, isopentyl, neopentyl, hexyl, etc.; straight or branched alkenyl group having 1 to 6 carbon atoms, such as ethenyl, 1-propenyl, allyl, 1-butenyl, 2-butenyl, 3-butenyl, pentenyl, hexenyl, etc.; straight or branched alkynyl group having 1 to 6 carbon atoms, such as ethynyl, propynyl, butynyl, pentynyl, hexynyl, etc.; alkoxy group having 1 to 6 carbon atoms, such as methoxy, ethoxy, propoxy, isopropoxy, butoxy, pentyloxy, hexyloxy, phenoxy, etc.; acyl group having 1 to 6 carbon atoms, such as formyl, acetyl, propionyl, butyryl, isobutyryl, valeryl, isovaleryl, pivaloyl, hexanoyl, etc.; carboxy group; carbamoyl group; and/or amino group, etc.

In $R_2$, $R_4$, $R_5$ and $R_6$ described above, the "halogen" means chlorine, fluorine, bromine, iodine, etc.; the "lower alkyl" means a straight or branched alkyl group having 1 to 6 carbon atoms such as methyl, ethyl, propyl, isopropyl, butyl, isobutyl, s-butyl, t-butyl, pentyl, isopentyl, neopentyl, hexyl, etc.; the "lower alkenyl" means a straight or branched alkenyl group such as ethenyl, 1-propenyl, allyl, 1-butenyl, 2-butenyl, 3-butenyl, pentenyl, hexenyl, etc.; the "lower alkynyl" means a straight or branched alkynyl group having 1 to 6 carbon atoms, such as ethynyl, propynyl, butynyl, pentynyl, hexynyl, etc.; the "lower alkoxy group" means an alkoxy group having 1 to 6 carbon atoms, such as methoxy, ethoxy, propoxy, isopropoxy, butoxy, pentyloxy, hexyloxy, phenoxy, etc.; the "lower acyl group" means an acyl group having 1 to 6 carbon atoms, such as formyl, acetyl, propionyl, butyryl, isobutyryl, valeryl, isovaleryl, pivaloyl, hexanoyl, etc. The "cycloalkyl group" in $R_4$, $R_5$ and $R_6$ means a cycloalkyl group having 3 to 8 carbon atoms, such as cyclopropyl, cyclobutyl, cyclopentyl, cyclohexyl, cycloheptyl, cyclooctyl, etc.

In the substituent(s) described above, the term "optionally substituted" means that these groups may optionally have 1 or more (e.g., 1 to 3) substituents, including a hydroxy group; nitro group; cyano group; halogen such as chlorine, fluorine, bromine, iodine, etc.; straight or branched alkyl group having 1 to 6 carbon atoms such as methyl, ethyl, propyl, isopropyl, butyl, isobutyl, s-butyl, t-butyl, pentyl, isopentyl, neopentyl, hexyl, etc.; straight or branched alkenyl group having 1 to 6 carbon atoms, such as ethenyl, 1-propenyl, allyl, 1-butenyl, 2-butenyl, 3-butenyl, pentenyl, hexenyl, etc.; straight or branched alkynyl group having 1 to 6 carbon atoms, such as ethynyl, propynyl, butynyl, pentynyl, hexynyl, etc.; alkoxy group having 1 to 6 carbon atoms, such as methoxy, ethoxy, propoxy, isopropoxy, butoxy, pentyloxy, hexyloxy, phenoxy, etc.; acyl group having 1 to 6 carbon atoms, such as formyl, acetyl, propionyl, butyryl, isobutyryl, valeryl, isovaleryl, pivaloyl, hexanoyl, etc.; carboxy group; carbamoyl group; and/or amino group, etc.

In $R_1$ and $R_3$ described above, the "protecting group" is not particularly limited and may be any group, as long as the group is appropriate as a protecting group of hydroxy group; the protecting group includes, for example, a lower acyl group, optionally substituted lower alkyl group, optionally substituted lower alkylsulfonyl group, optionally substituted lower alkoxycarbonyl group, a substituted silyl group, etc. The "lower acyl group", "lower alkyl group", "lower alkoxy group", optionally substitutable "substituents," etc. are as defined in the foregoing paragraph.

The combined compound of the ferrocene compound and the VD compound, which is obtained by reacting the ferrocene compound of the present invention described above with a VD compound, is useful as, e.g., a reference standard in measuring the VD compound by LC/ESI-MS/MS, etc.

Also in measuring a VD compound present in a sample, the ferrocene compound of the present invention may be combined with the VD compound, following the method described above. Herein, the sample is preferably a sample from a living body. The sample from the living body means body fluids (blood, lymphatic fluid, spinal fluid), urine, etc., preferably plasma, serum or urine. Furthermore, the term from the living body means preferably from mammals, more preferably from human, monkey, dog, rabbit, guinea pig, rat or mouse. Where a VD compound present in a sample from the living body is measured, necessary pre-treatments like protein precipitation by known techniques such as protein precipitation with ethanol, etc. are made, then the ferrocene compound of the present invention is combined with the VD compound present in the sample as in the method described above, and the resulting combined compound of the ferrocene compound and the VD compound, which is obtained by reacting the ferrocene compound of the present invention with the VD compound can be used for the following measurement.

Herein, it is preferred that at this stage the sample is subjected to protein precipitation as a pre-treatment of the sample and then to solid phase extraction of the sample before the ferrocene compound of the present invention is reacted with the VD compound present in the sample. It is also preferred that after the ferrocene compound of the present invention is reacted with the VD compound present in the sample, the sample is subjected to solid phase extraction. Particularly preferably, after the sample is subjected to protein precipitation and then to solid phase extraction, the ferrocene compound of the present invention is reacted with the VD compound present in the sample, followed by solid phase extraction of the sample again. The solid phase extraction after protein precipitation of the sample and prior to the reaction of the ferrocene compound of the present invention with the VD compound present in the sample is preferably performed using a solid phase extraction cartridge on a normal phase system, particularly preferably using a solid phase extraction cartridge on a silica gel system. The solid phase extraction after the reaction of the ferrocene compound of the present invention with the VD compound in the sample is carried out preferably using a solid phase extraction cartridge on a reversed phase system.

The thus obtained combined compound of the ferrocene compound and the VD compound is applied on LC/MS for the measurement. Herein, LC/MS means the measurement techniques or measurement instruments, utilizing or applying the measurement principle by LC/MS (liquid chromatography/mass spectrometry) thereto, specifically including the measurement techniques or measurement instruments by liquid chromatography/mass spectrometry (LC/MS) and tandem liquid chromatography/mass spectrometry/mass spectrometry (LC/MS/MS), as well as these techniques in combination with electrospray ionization (ESI) and atmospheric pressure chemical ionization (APCI). Among them, it is particularly preferred to apply liquid chromatography/electrospray ionization-mass spectrometry/mass spectrometry (LC/ESI-MS/MS) in performing the measurement method of the present invention.

According to the measurement by LC/ESI-MS/MS, the residue containing the combined compound of the ferrocene compound and the VD compound obtained as described above is dissolved in a mobile phase and the solution is injected into LC/ESI-MS/MS, followed by the measurement. Herein, specific operations including measurement conditions of LC/ESI-MS/MS in each measurement, and the like may be appropriately adjusted/set forth by known technique, depending on the amount or kind of analyte sample, the amount or kind of a VD compound present in a sample, sensitivity required for measurement, kind of the ferrocene compound of the present invention used as a derivatization agent, construction of LC/ESI-MS/MS instruments used for measurement, etc. Specifically, conditions for MRM (Multiple Reaction Monitoring) of the combined compound of the ferrocene compound and a VD compound are closely examined to appropriately set various conditions, and also set conditions for LC enabling to efficient ionization. In measuring the concentration in a biological sample, an analyte of known concentrations with concentration gradients is added to a blank sample, internal standard (I.S., preferably an analyte labeled with a stable isotope) is added to each of the mixtures, which are measured, respectively. The peak area ratio (or peak height ratio) of the analyte to I.S. is determined. In relation to the added concentration, a calibration curve is prepared and from the calibration curve and the peak area ratio (or peak height ratio) of the analyte, the concentration in a biological sample is calculated. For the details of these techniques, reference can be made to the latest issue of Mass Spectrometry (first edition, published by Kagaku Dojin, edited by Toshimitsu Niwa, 1995), Biological Mass Spectrometry (published by Kagaku Dojin, edited by Tamio Ueno, Kazuo Hirayama, Ken-ichi Harada, 1997), LC/MS-NO-JISSAI (Practice of LC/MS) (first edition, published by Kodansha Scientific, edited by Ken-ichi Harada, Hisao Oka, 1996), etc.

The method of the present invention for measuring a VD compound thus performed is a measurement method with a higher sensitivity than in conventional techniques. Furthermore, in the measurement of a VD compound having no hetero atom such as an ester bond, an ether bond, a thioether bond, an amide bond, etc. in the molecule (specifically, $VD_3$, calcipotriol, $1\alpha, 25(OH)_2D_3$, ALF, falecalcitriol, EB1089 and Compound A described above, etc.) which were measured with an insufficient sensitivity in conventional methods, the measurement method of the present invention is a high-sensitivity method which can achieve the sensitivity of higher even by several hundred times than in conventional methods. Accordingly, the high-sensitivity measurement method is applicable to all VD compounds, not only to VD compounds having hetero atoms such as an ester bond, an ether bond, a thioether bond, an amide bond, etc. (specifically, OCT, ED-71, etc. described above) but also to VD compounds having no such hetero atom.

The present invention will be described in more detail with reference to preferred working examples, but is not limited to these working examples.

EXAMPLES

In EXAMPLES below, nuclear magnetic resonance (NMR) was measured using EX-270 (manufactured by JEOL). Also, high performance liquid chromatograph Alliance 2790 (manufactured by Waters Co.) and a quadrupole mass spectrometer Quattro LC (manufactured by Micromass UK Ltd.) were used as electrospray ionization LC/MS/MS (LC/ESI-MS/MS). For data analysis, Masslynx Ver. 3.3 (manufactured by Micromass UK, Inc.) and Microsoft Excel 2000 (manufactured by Microsoft Corp.) were used.

Example 1

Synthesis of Derivatization Agent

Example 1-1

Synthesis of 4-(ferrocenylmethyl)-1,2,4-triazoline-3,5-dione (FMTAD)

(1) Synthesis of ethyl 3-(ferrocenylmethyl)carbamoylcarbazate

Under ice cooling, 0.57 mL (4 mmols) of triethylamine was added to a mixture of 0.5 g (2 mmols) of ferroceneacetic acid (manufactured by Tokyo Kasei Kogyo Co., Ltd.), 0.44 mL (2 mmols) of diphenylphosphyrylazide and 4 mL of toluene. The mixture was stirred at room temperature for 30 minutes. The reaction mixture was diluted with dichloromethane. The dilution was washed sequentially with a 1% hydrochloric acid aqueous solution and saturated sodium hydrogencarbonate solution. After drying over anhydrous magnesium sulfate, the organic layer was filtered and concentrated under reduced pressure to give 4 mL of the toluene solution. To the toluene solution obtained, 2 mL of toluene was added and 0.32 g (3 mmols) of ethyl carbazate was added to the mixture while stirring at room temperature. The mixture was then heated under reflux for 3 hours and diluted with dichloromethane. The dilution was washed sequentially with a 1% hydrochloric acid aqueous solution and saturated sodium hydrogencarbonate solution. After drying over anhydrous magnesium sulfate, the organic layer was filtered and concentrated under reduced pressure. The resulting residue was purified by silica gel column chromatography (chloroform:methanol=20:1) to give 0.55 g (78%) of ethyl 3-(ferrocenylmethyl)carbamoylcarbazate as a yellow oily substance.

$^1$H NMR (CDCl$_3$) δ: 1.27 (3H, t, J=7.3 Hz), 4.0–4.3 (13H, m), 5.59 (1H, m), 6.59 (1H, s), 6.66 (1H, s)

(2) Synthesis of 4-(ferrocenylmethyl)urazole

A mixture of 0.55 g (1.6 mmol) of ethyl 3-(ferrocenylmethyl)carbamoylcarbazate obtained in (1) above, 460 mg (3.3 mmols) of potassium carbonate and 16 mL of ethanol was heated under reflux for 14 hours. After filtration, the reaction mixture was concentrated under reduced pressure. The residue obtained was purified by silica gel column chromatography (chloroform:methanol=10:1) to give 376 mg (78%) of 4-(ferrocenylmethyl)urazole.

$^1$H NMR (THF-d$_8$) δ: 3.86 (2H, m), 3.96 (5H, s), 4.10 (2H, m), 4.13 (2H, s), 8.38 (2H, brs)

(3) Synthesis of 4-(ferrocenylmethyl)-1,2,4-triazoline-3,5-dione

To a mixture of 10 mg (0.033 mmol) of 4-(ferrocenylmethyl)urazole obtained in (2) above and 0.5 mL of tetrahydrofuran-d$_8$, 11 mg (0.034 mmol) of iodobenzene diacetate was added at room temperature. The mixture was stirred for 2 hours to give the tetrahydrofuran solution of 4-(ferrocenylmethyl)-1,2,4-triazoline-3,5-dione.

$^1$H NMR (THF-d$_8$) δ: 3.98 (2H, m), 4.04 (5H, s), 4.16 (2H, m), 4.38 (2H, s)

Example 1-2

Synthesis of 4-ferrocenyl-1,2,4-triazoline-3,5-dione (FTAD)

(1) Synthesis of ethyl 3-ferrocenylcarbamoylcarbazate

Under ice cooling, 0.6 mL (4.3 mmols) of triethylamine was added to a mixture of 0.5 g (2.17 mmols) of ferrocenecarboxylic acid (manufactured by Tokyo Kasei Kogyo Co., Ltd.), 0.47 mL (2.17 mmols) of diphenylphosphorylazide and 4 mL of toluene and the mixture was stirred at room temperature for 30 minutes. The reaction mixture was diluted with dichloromethane. The dilution was washed sequentially with a 1% hydrochloric acid aqueous solution and saturated sodium hydrogencarbonate solution. After drying over anhydrous magnesium sulfate, the organic layer was filtered and concentrated under reduced pressure to give 4 mL of the toluene solution. To the toluene solution obtained, 2 mL of toluene was added and 0.34 g (3.27 mmols) of ethyl carbazate was added to the mixture while stirring at room temperature. The reaction mixture was heated under reflux for an hour and then diluted with dichloromethane. The dilution was washed sequentially with a 1% hydrochloric acid aqueous solution and saturated sodium hydrogencarbonate solution. After drying over anhydrous magnesium sulfate, the organic layer was filtered and then concentrated under reduced pressure. The resulting residue was washed with a hexane-dichloromethane (1:1) mixture to give 0.52 g (72%) of ethyl 3-ferrocenylcarbamoylcarbazate as yellow powders.

$^1$H NMR (CDCl$_3$) δ: 1.31 (3H, t, J=7.1 Hz), 4.03 (2H, s), 4.20 (5H, s), 4.25 (2H, q, J=7.1 Hz), 4.47 (2H, s), 6.24 (1H, brs), 6.40 (1H, brs), 6.55 (1H, brs)

MS (ESI): m/z 332 (M$^+$+1), 331 (M$^+$)

(2) Synthesis of 4-ferrocenylurazole

A mixture of 0.52 g (1.57 mmol) of ethyl 3-ferrocenylcarbamoylcarbazate obtained in (1) above, 434 mg (3.14 mmols) of potassium carbonate and 16 mL of ethanol was heated under reflux for 13 hours. The mixture was concentrated under reduced pressure and then rendered acidic with 2N hydrochloric acid. Thereafter, the mixture was extracted with a dichloromethane-methanol (10:1) solvent mixture. After washing with water, the organic layer was dried over anhydrous magnesium sulfate, filtered and then concentrated under reduced pressure. The resulting residue was purified by silica gel column chromatography (dichloromethane-methanol=20:1) to give 320 mg (71%) of 4-ferrocenylurazole.

$^1$H NMR (THF-d$_8$) δ: 3.87 (2H, t, J=2.0 Hz), 3.96 (5H, s), 4.86 (2H, t, J=2.0 Hz), 8.64 (2H, brs)

MS (ESI): m/z 286 (M$^+$+1), 285 (M$^+$)

(3) Synthesis of 4-ferrocenyl-1,2,4-triazoline-3,5-dione

To a mixture of 10 mg (0.035 mmol) of 4-ferrocenylurazole obtained in (2) above and 0.5 mL of tetrahydrofuran-d$_8$, 11 mg (0.034 mmol) of iodobenzene diacetate was added at room temperature, followed by stirring for an hour. Thus, the tetrafuran solution of 4-ferrocenyl-1,2,4-triazoline-3,5-dione was obtained.

$^1$H NMR (THF-d$_8$) δ: 4.0–4.1 (7H, m), 4.66 (2H, t, J=2.0 Hz)

(4) Synthesis (2) of 4-ferrocenyl-1,2,4-triazoline-3,5-dione

To a mixture of 10 mg (0.035 mmol) of 4-ferrocenylurazole obtained in (2) above and 0.5 mL of 1,4-dioxane-$d_8$, 11 mg (0.034 mmol) of iodobenzene diacetate was added at room temperature, followed by stirring for 2 hours. Thus, the 1,4-dioxane solution of 4-ferrocenyl-1,2,4-triazoline-3,5-dione was obtained.

$^1$H NMR (1,4-dioxane-$d_8$) δ: 4.2–4.3 (7H, m), 4.87 (2H, m)

Example 2

Synthesis of the Combined Compound of a Derivatization Agent and a Vitamin D Compound

Example 2-1

Synthesis of the alfacalcidol/4-(ferrocenylmethyl)-1,2,4-triazoline-3,5-dione adduct (ALF-FMTAD)

With reference to EXAMPLE 1-1, 5 mg (0.016 mmol) of iodobenzene diacetate was added to a mixture of 5 mg (0.017 mmol) of 4-(ferrocenylmethyl)urazole and 0.25 mL of tetrahydrofuran at room temperature. The mixture was stirred for 2 hours to give the tetrahydrofuran solution of 4-(ferrocenylmethyl)-1,2,4-triazoline-3,5-dione. A tetrahydrofuran (0.25 mL) solution of 1 mg (0.0025 mmol) of alfacalcidol prepared in accordance with the method described in Japanese Patent Publication (KOKAI) No. 48-62750, Tetrahedron Lett., 1973, 2339 and Tetrahedron, 30, 2701 (1974) was added to the resulting solution, followed by stirring at room temperature for an hour. The resulting mixture was concentrated under reduced pressure and the residue obtained was purified by thin layer silica gel chromatography (hexane:ethyl acetate=1:2) to give 1 mg (57%) of the titled alfacalcidol/4-(ferrocenylmethyl)-1,2,4-triazoline-3,5-dione adduct (ALF-FMTAD) as a yellow oily substance.

$^1$H NMR (CDCl$_3$) δ: 0.4–0.6 (3H, m), 3.6–3.8 (1H, m), 4.0–4.6 (16H, m), 4.6–4.8 (1H, m), 4.8–4.9 (1H, m)

Example 2-2

Synthesis of the alfacalcidol/4-ferrocenyl-1,2,4-triazoline-3,5-dione adduct (ALF-FTAD)

With reference to EXAMPLE 1-2, 4.5 mg (0.014 mmol) of iodobenzene diacetate was added to a mixture of 5 mg (0.017 mmol) of 4-ferrocenylurazole and 0.25 mL of tetrahydrofuran at room temperature, followed by stirring for an hour. Thus, the tetrahydrofuran solution of 4-ferrocenyl-1,2,4-triazoline-3,5-dione was obtained. A tetrahydrofuran (0.25 mL) solution of 1 mg (0.0025 mmol) of alfacalcidol prepared in accordance with the method described in Japanese Patent Publication (KOKAI) No. 48-62750, Tetrahedron Lett., 1973, 2339 and Tetrahedron, 30, 2701 (1974) was added to the solution obtained. The mixture was stirred at room temperature for an hour. The reaction mixture was concentrated under reduced pressure and the residue obtained was purified by thin layer silica gel chromatography (hexane:ethyl acetate=1:2) to give 1 mg (57%) of the titled alfacalcidol/4-ferrocenyl-1,2,4-triazoline-3,5-dione adduct (ALF-FTAD) as a yellow oily substance.

$^1$H NMR (CDCl$_3$) δ: 0.54 (3H, s), 0.85 (6H, d, J=6.3 Hz), 0.89 (3H, d, J=5.3 Hz), 3.79 (1H, brd, J=15.5 Hz), 4.0–4.4 (11H, m), 4.66 (1H, d, J=17.6 Hz), 4.9–5.1 (3H, m)

EXAMPLE 2-3

Synthesis of the cholecalciferol/4-(ferrocenylmethyl)-1,2,4-triazoline-3,5-dione adduct (VD$_3$-FMTAD)

With reference to EXAMPLE 1-1, 11 mg (0.034 mmol) of iodobenzene diacetate was added to a mixture of 10 mg (0.033 mmol) of 4-(ferrocenylmethyl)urazole and 0.5 mL of tetrahydrofuran-$d_8$ at room temperature. The mixture was stirred for 2 hours to give the tetrahydrofuran solution of 4-(ferrocenylmethyl)-1,2,4-triazoline-3,5-dione. A tetrahydrofuran (0.5 mL) solution of 5 mg (0.013 mmol) of cholecalciferol (VD$_3$, manufactured by Solvay Pharmaceutical, Co.) was added to the resulting solution, followed by stirring at room temperature for an hour. The reaction mixture was concentrated under reduced pressure and the residue obtained was purified by thin layer silica gel chromatography (hexane:ethyl acetate=1:2) to give 8 mg (90%) of the titled cholecalciferol/4-(ferrocenylmethyl)-1,2,4-triazoline-3,5-dione adduct (VD$_3$-FMTAD) as a yellow oily substance.

$^1$H NMR (CDCl$_3$) δ: 0.47 (3H, s), 0.87 (6H, d, J=6.4 Hz), 0.92 (3H, d, J=5.9 Hz), 3.71 (1H, brd, J=15.2 Hz), 4.0–4.5 (15H, m), 4.60 (1H, d, J=9.9 Hz), 4.86 (1H, d, J=9.6 Hz)

Example 2-4

Synthesis of the cholecalciferol/4-ferrocenyl-1,2,4-triazoline-3,5-dione adduct (VD$_3$-FTAD)

With reference to EXAMPLE 1-2, 11 mg (0.034 mmol) of iodobenzene diacetate was added to a mixture of 10 mg (0.035 mmol) of 4-ferrocenylurazole and 0.5 mL of tetrahydrofuran at room temperature. The mixture was stirred for an hour to give the tetrahydrofuran solution of 4-ferrocenyl-1,2,4-triazoline-3,5-dione. A tetrahydrofuran (0.5 mL) solution of 10 mg (0.026 mmol) of cholecalciferol (VD$_3$, manufactured by Solvay Pharmaceutical, Co.) was added to the solution obtained, followed by stirring at room temperature for an hour. The resulting mixture was concentrated under reduced pressure and the residue obtained was purified by thin layer silica gel chromatography (hexane:ethyl acetate=2:1) to give 11 mg (63%) of the titled cholecalciferol/4-ferrocenyl-1,2,4-triazoline-3,5-dione adduct (VD$_3$-FTAD) as a yellow oily substance.

$^1$H NMR (CDCl$_3$) δ: 0.60 (3H, s), 0.85 (6H, d, J=6.6 Hz), 0.92 (3H, d, J=5.8 Hz), 3.81 (1H, brd, J=15.5 Hz), 4.0–4.3 (11H, m), 4.73 (1H, d, J=9.9 Hz), 4.9–5.0 (2H, m), 5.05 (1H, d, J=1.5 Hz)

Comparative Example 2-1

Synthesis of 3-(ferrocenylcarbamoyloxy)cholecalciferol (VD$_3$-ferrocene carbamate)

Under ice cooling, 0.015 mL (0.108 mmol) of triethylamine was added to a mixture of 10 mg (0.043 mmol) of ferrocenecarboxylic acid, 0.01 mL (0.046 mmol) of diphenylphosphyrylazide and 0.5 mL of toluene. The mixture was stirred at room temperature for 30 minutes. The reaction mixture was diluted with dichloromethane and the dilution was washed with 1% hydrochloric acid and saturated sodium bicarbonate aqueous solution. After the organic layer was dried over anhydrous magnesium sulfate and filtered, dichloromethane was distilled off under reduced pressure to give the unpurified toluene solution. To the toluene solution obtained, 10 mg (0.026 mmol) of cholecalciferol (VD$_3$, manufactured by Solvay Pharmaceutical, Co.) was added and the mixture was stirred at 100° C. for an hour. The reaction mixture was concentrated under reduced pressure. The residue obtained was purified by thin layer silica gel column chromatography (hexane:ethyl acetate=5:1) to give 6 mg of 3-(ferrocenylcarbamoyloxy)cholecalciferol (VD$_3$-ferrocene carbamate) as a yellow oily substance.

$^1$H NMR (CDCl$_3$) δ: 0.55 (3H, s), 0.87 (6H, d, J=6.4 Hz), 0.92 (3H, d, J=6.1 Hz), 3.99 (2H, brs), 4.17 (7H, brs), 4.48 (2H, brs), 4.86 (1H, s), 4.94 (1H, brs), 5.08 (1H, s), 5.7–5.9 (1H, m), 6.06 (1H, d, J=11.1 Hz), 6.25 (1H, d, J=11.1 Hz)

Example 3

Determination of the Combined Compound of a Derivatization Agent and a Vitamin D Compound

Example 3-1

Determination of the alfacalcidol/4-(ferrocenylmethyl)-1,2,4-triazoline-3,5-dione adduct (ALF-FMTAD) and the alfacalcidol/4-ferrocenyl-1,2,4-triazoline-3,5-dione adduct (ALF-FTAD)

The alfacalcidol/4-(ferrocenylmethyl)-1,2,4-triazoline-3,5-dione adduct (ALF-FMTAD) prepared with reference to EXAMPLE 2-1 and the alfacalcidol/4-ferrocenyl-1,2,4-triazoline-3,5-dione adduct (ALF-FTAD) prepared with reference to EXAMPLE 2-2 were dissolved, respectively, in 50 μL of a mobile phase (10 mmol/L ammonium acetate/acetonitrile (1:9, v/v)) and 20 μL of the solution was injected into LC/ESI-MS/MS. Using Capcell Pak C18 UG-120 (5 μm, 150×2.0 mm i.d.: manufactured by Shiseido Co., Ltd.) as HPLC column, ESI mass spectra of ALF-FMTAD and ALF-FTAD were measured in a positive ion mode to give the molecular ions [M]$^+$ at m/z 697 and m/z 683 as the base peaks. An example of the measurement results is shown in FIG. 1. When the corn voltage was set at 70V and 66V, respectively, the intensity reached the maximum.

Figure 2:
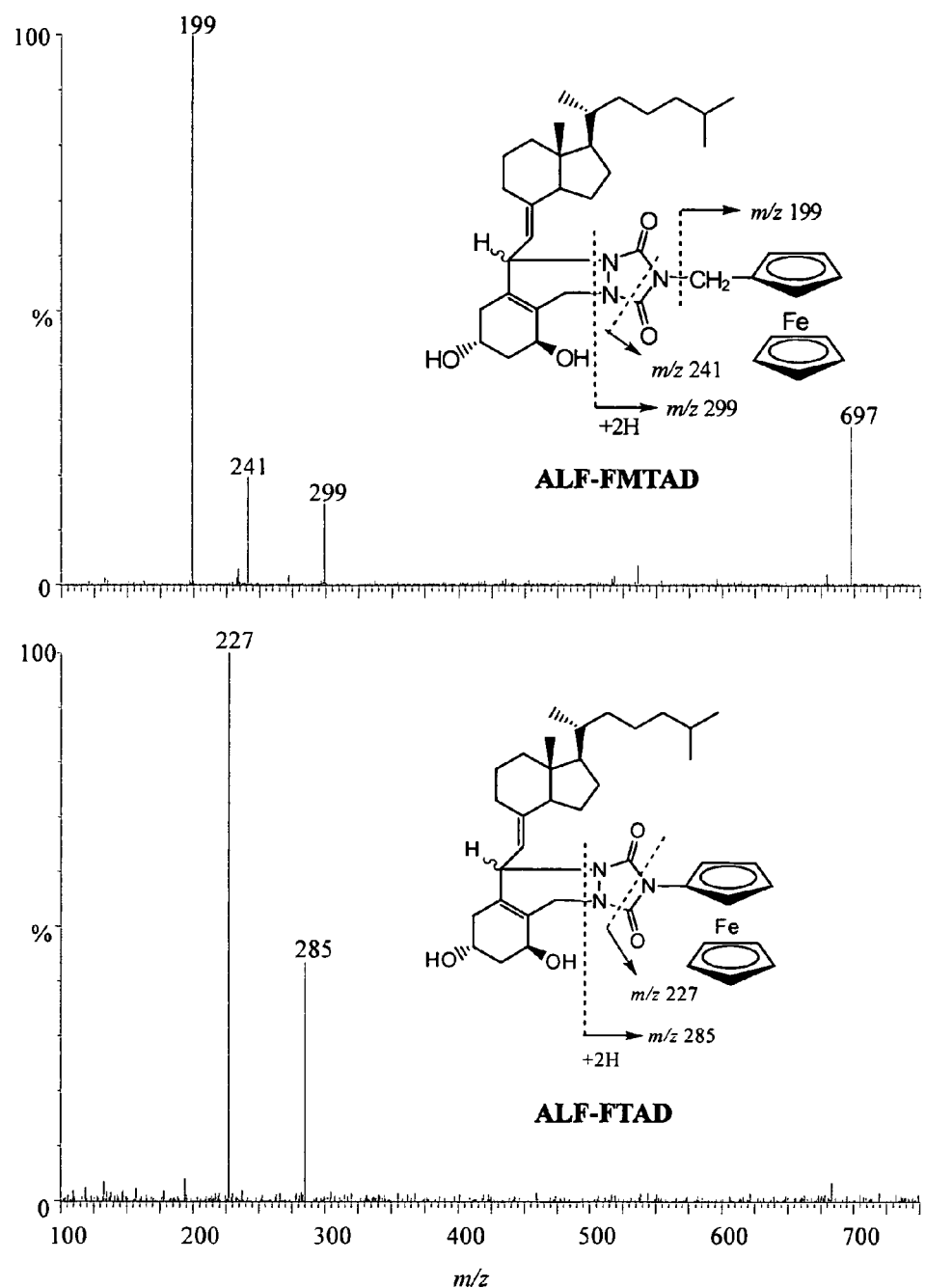
FIG. 2 illustrates an example of the results when the product ion spectra were measured using molecular ions [M]$^+$ of ALF-FMTAD and molecular ions [M]$^+$ of ALF-FTAD as precursor ions.
Figure 3:
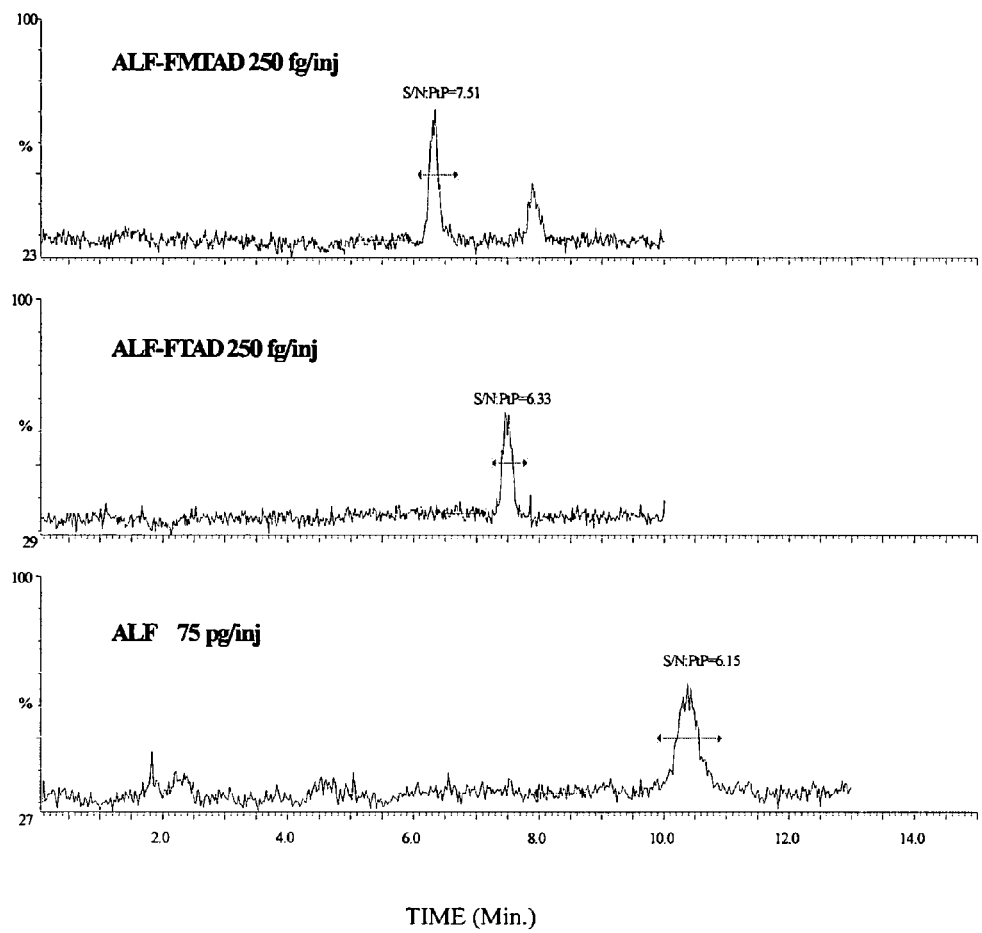
FIG. 3 illustrates an example of the results in direct assay (control) of ALF-FMTAD, ALF-FTAD and ALF under the optimized conditions for measurement by LC/ESI-MS/MS.

The product ion spectrum was assayed using these molecular ions as precursor ions and strong fragment ions having the ferrocene skeleton were given at m/z 199 and m/z 227, respectively. An example of the assay results is shown in FIG. 2. After close examination of MRM (Multiple Reaction Monitoring) conditions for ALF-FMTAD and ALF-FTAD, the collision energy was set to 44 eV using m/z 697 [M]$^+$>199 [M—C$_{29}$H$_{44}$O$_4$N$_3$]$^+$ and m/z 683 [M]$^+$>227 [M—C$_{28}$H$_{44}$O$_3$N$_2$]$^+$ as monitoring channels, respectively, so that ultra-sensitive measurement could be made to give the sensitivity of 250 fg (359 amol, 366 amol)/inj (S/N ratio was approximately 6 to 8) in both cases. On the other hand, the sensitivity of alfacalcidol (ALF) when directly determined was 75 pg (188 fmol)/inj (S/N ratio was about 6), indicating that the measurement method of the present invention was higher by about 300 times than in the direct assay. An example of these measurement results is shown in FIG. 3.

Example 3-2

Determination of the cholecalciferol/4-(ferrocenylmethyl)-1,2,4-triazoline-3,5-dione adduct (VD$_3$-FMTAD) and the cholecalciferol/4-ferrocenyl-1,2,4-triazoline-3,5-dione adduct (VD$_3$-FTAD)

Figure 4:
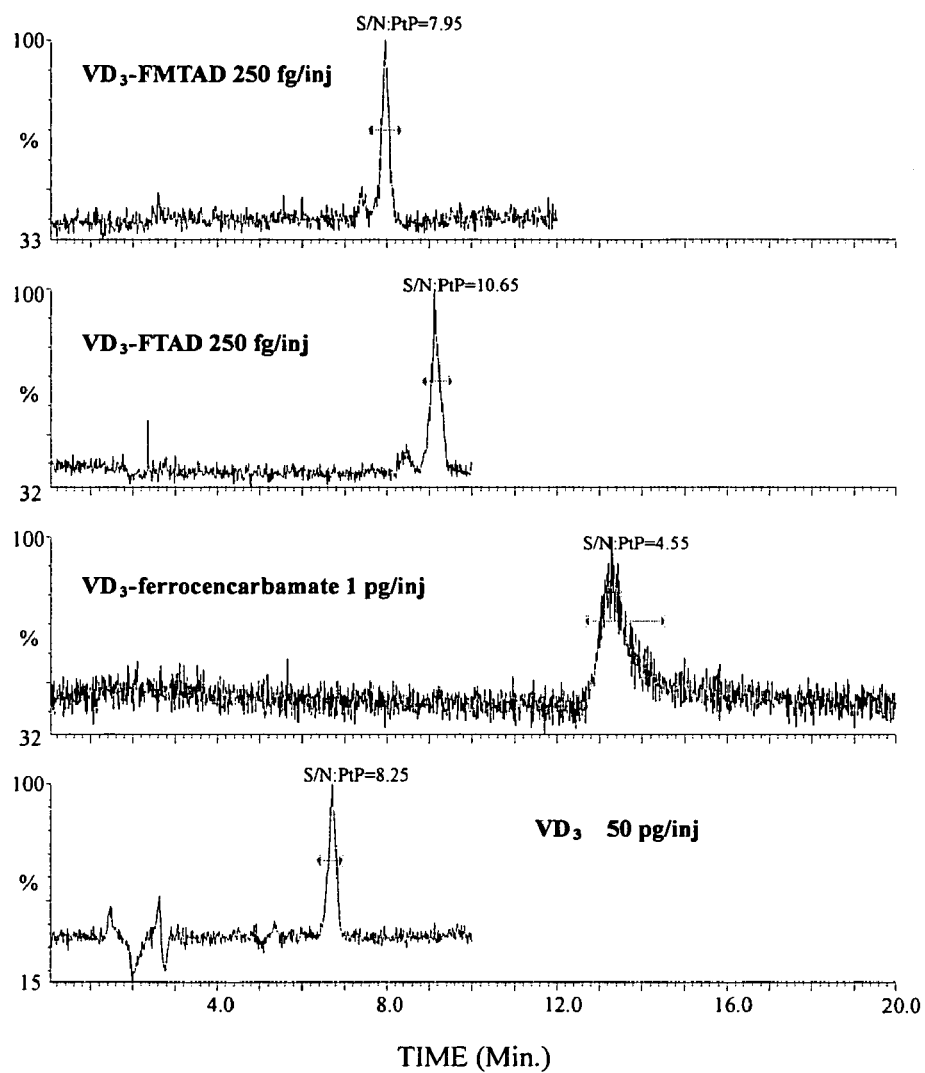
FIG. 4 illustrates an example of the results in direct assay (control) of $VD_3$-FMTAD, $VD_3$-FTAD and VD3 and in measurement of $VD_3$-ferrocene carbamates (control), under the optimized conditions for measurement by LC/ESI-MS/MS.

Using the cholecalciferol/4-(ferrocenylmethyl)-1,2,4-triazoline-3,5-dione adduct (VD$_3$-FMTAD) synthesized with reference to EXAMPLE 2-3 and the cholecalciferol/4-ferrocenyl-2,4-triazoline-3,5-dione adduct (VD$_3$-FTAD) synthesized with reference to EXAMPLE 2-4, the conditions for measurement were optimized as in EXAMPLE 3-1 so that the sensitivity of 250 fg (367 amol, 375 amol)/inj (S/N ratio of approximately 8 to 11) was obtained. On the other hand, the sensitivity of cholecalciferol (VD$_3$) when directly determined and the sensitivity of 3-(ferrocenylcarbamoyloxy)cholecalciferol (VD$_3$-ferrocene carbamate) (cf. COMPARATIVE EXAMPLE 2-1) were 50 pg (130 fmol)/inj (S/N ratio of about 8) and 1 pg (1.64 fmol)/inj (S/N ratio of about 5), indicating that the measurement method of the present invention was higher by about 200 times than in the direct assay and by 4 times or more, even when compared to the measurement by derivatization with the ferrocene carbamate. An example of these measurement results is shown in FIG. 4.

Example 3-3

Determination of the ED-71/4-(ferrocenylmethyl)-1,2,4-triazoline-3,5-dione adduct (ED-71-FMTAD) and the compound described in WO 02/13832, Example 6 (Compound A)/4-(ferrocenylmethyl)-1,2,4-triazoline-3,5-dione adduct (Compound A-FMTAD)

Using the ED-71/4-(ferrocenylmethyl)-1,2,4-triazoline-3,5-dione adduct (ED-71-FMTAD) synthesized with reference to EXAMPLE 2 and the compound described in WO 02/13832, EXAMPLE 6 (Compound A)/4-(ferrocenylmethyl)-1,2,4-triazoline-3,5-dione adduct (Compound A-FMTAD), the conditions for measurement were optimized as in EXAMPLE 3-1 so that the sensitivities of 300 fg (381 amol)/inj and 500 fg (668 amol)/inj were obtained. On the other hand, the sensitivities of ED-71 and Compound A when directly determined were 10 pg (20 fmol)/inj and 50 pg (111 μmol/inj, respectively.

The results of EXAMPLES 3-1,3-2 and 3-3 described above are summarized in TABLE 1.

TABLE 1

| Compound | Conditions for MRM | Sensitivity of determination (per injection) | S/N Ratio |
|---|---|---|---|
| ALF (direct assay, control) | m/z 418 [M + NH$_4$]$^+$ > 383 [M–H$_2$O + H]$^+$ | 75 pg (188 fmol) | 6 |
| ALF-FTAD | m/z 683 [M]$^+$ > 227 [M–C$_{28}$H$_{44}$O$_3$N$_2$]$^+$ | 250 fg (366 amol) | 6 |
| ALF-FMTAD | m/z 697 [M]$^+$ > 199 [M–C$_{29}$H$_{44}$O$_4$N$_3$]$^+$ | 250 fg (359 amol) | 8 |

TABLE 1-continued

| Compound | Conditions for MRM | Sensitivity of determination (per injection) | S/N Ratio |
|---|---|---|---|
| $VD_3$ (direct assay, control) | m/z 385 $[M + H]^+$ > 367 $[M–H_2O + H]^+$ | 50 pg (130 fmol) | 8 |
| $VD_3$-Ferrocene carbamate (control) | m/z 611 $[M]^+$ > 245 $[M–C_{27}H_{42}]^+$ | 1 pg (1.64 fmol) | 5 |
| $VD_3$-FTAD | m/z 667 $[M]^+$ > 227 $[M–C_{28}H_{44}O_2N_2]^+$ | 250 fg (375 amol) | 11 |
| $VD_3$-FMTAD | m/z 681 $[M]^+$ > 199 $[M–C_{29}H_{44}O_3N_3]^+$ | 250 fg (367 amol) | 8 |
| ED-71 (direct assay, control) | m/z 508 $[M + NH_4]^+$ > 397 $[M–C_3H_8O_2–H_2O + H]^+$ | 10 pg (20 fmol) | 10 |
| ED-71-FMTAD | m/z 787 $[M]^+$ > 199 $[M–C_{33}H_{50}O_7N_3]^+$ | 300 fg (381 amol) | 10 |
| Compound A (direct assay, control) | m/z 470 $[M + NH_4]^+$ > 435 $[M–H_2O + H]^+$ | 50 pg (111 fmol) | 8 |
| Compound A-FMTAD | m/z 749 $[M]^+$ > 199 $[M–C_{32}H_{44}O_5N_3]^+$ | 500 fg (668 amol) | 6 |

Example 4

Measurement of Vitamin D Compounds in Biological Samples

Example 4-1

Determination of Alfacalcidol (ALF) in Rat Plasma by Derivatization with FMTAD (1) Preparation of Rat Blank Plasma Blood was collected from SD strain intact rats (SPF grade, purchased from Slc, Inc.) using sodium heparin as an anticoagulant and centrifuged. The plasma obtained from several individuals were mixed and used. Pooled plasma were stored at −20° C. or below.

(2) Study of Calibration Lower Limit for Alfacalcidol (ALF) (Derivatization with FMTAD)

Figure 5:
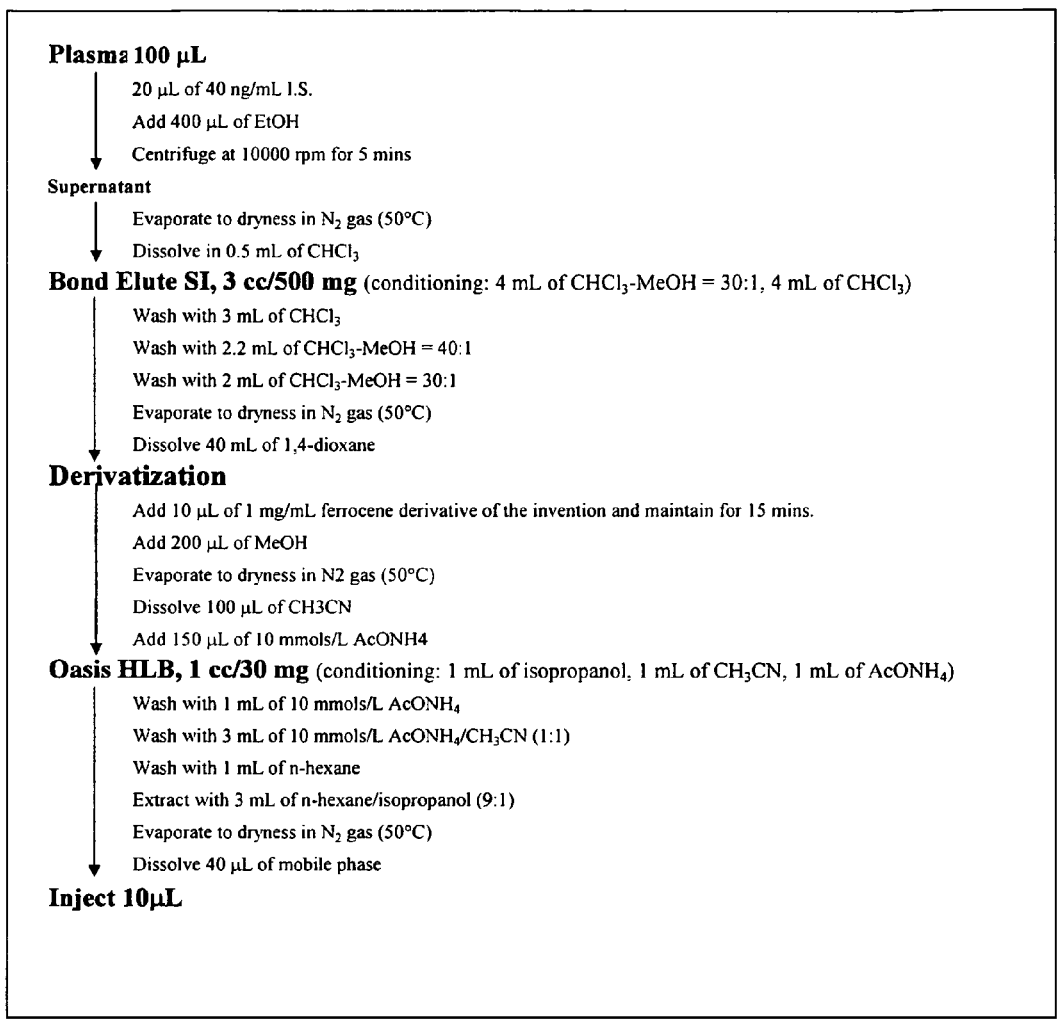
FIG. 5 illustrates an example of specific treatment schemes for pre-treatment in the measurement method of the present invention, when rat plasma was used as a sample.

A solution of alfacalcidol (ALF) in ethanol prepared by the procedure described in Japanese Patent Publication (KOKAI) No. 48-62750, Tetrahedron Lett., 1973, 2339 and Tetrahedron, 30, 2701 (1974) was added to 100 μL of rat blank plasma to prepare calibration sample solutions of 0, 0.08, 0.25, 0.8, 2.5, 8 and 25 ng/mL. To 100 μL of the solution of each concentration, 20 μL of 40 ng/mL $d_4$-ALF prepared in accordance with the procedure described in Chem. Pharm. Bull., 48, 215 (2000) was added as an internal standard (I.S.). After protein precipitation with ethanol and solid phase extraction through a solid phase extraction cartridge (Bond Elut SI, 3 cc, 500 mg: manufactured by Varian Inc.) were performed, the extract was subjected to derivatization with FMTAD. After the derivatization, solid phase extraction was again performed through a solid phase extraction cartridge (Oasis HLB, 1 cc, 30 mg: manufactured by Waters, Inc.) followed by evaporation to dryness in nitrogen. The residue was then dissolved in 40 μL of a mobile phase and 10 μL of the solution was injected into LC/ESI-MS/MS. A specific treatment scheme for the sample pretreatment is shown in FIG. 5. Determination conditions for LC/ESI-MS/MS are shown in TABLE 2.

TABLE 2

Determination conditions for ALF-FMTAD:

| | |
|---|---|
| Column: | Capcell Pak C18 UG-120 (5 μm, 150 × 2.0 mm i.d.) |
| Mobile phase: | Solution A: 10 mmol/L ammonium acetate Solution B: acetonitrile (A: 15%, B: 85%) |
| Column temperature: | 30° C. |
| Flow rate: | 0.2 mL/min. |
| Ionization mode: | ESI (+) |
| Capillary voltage: | 2.5 kV |
| Cone Voltage: | 70 V |
| Source block temperature: | 150° C. |
| Desolvator temperature: | 450° C. |
| Collision energy: | 46 eV |

Conditions for MRM (Multiple Reaction Monitoring):

ALF-FMTAD: m/z 697 $[M]^+$ > 199 $[M–C_{29}H_{44}O_4N_3]^+$
$d_4$-ALF-FMTAD: m/z 701 $[M]^+$ > 199 $[M–C_{29}H_{40}D_4O_4N_3]^+$

Figure 6:
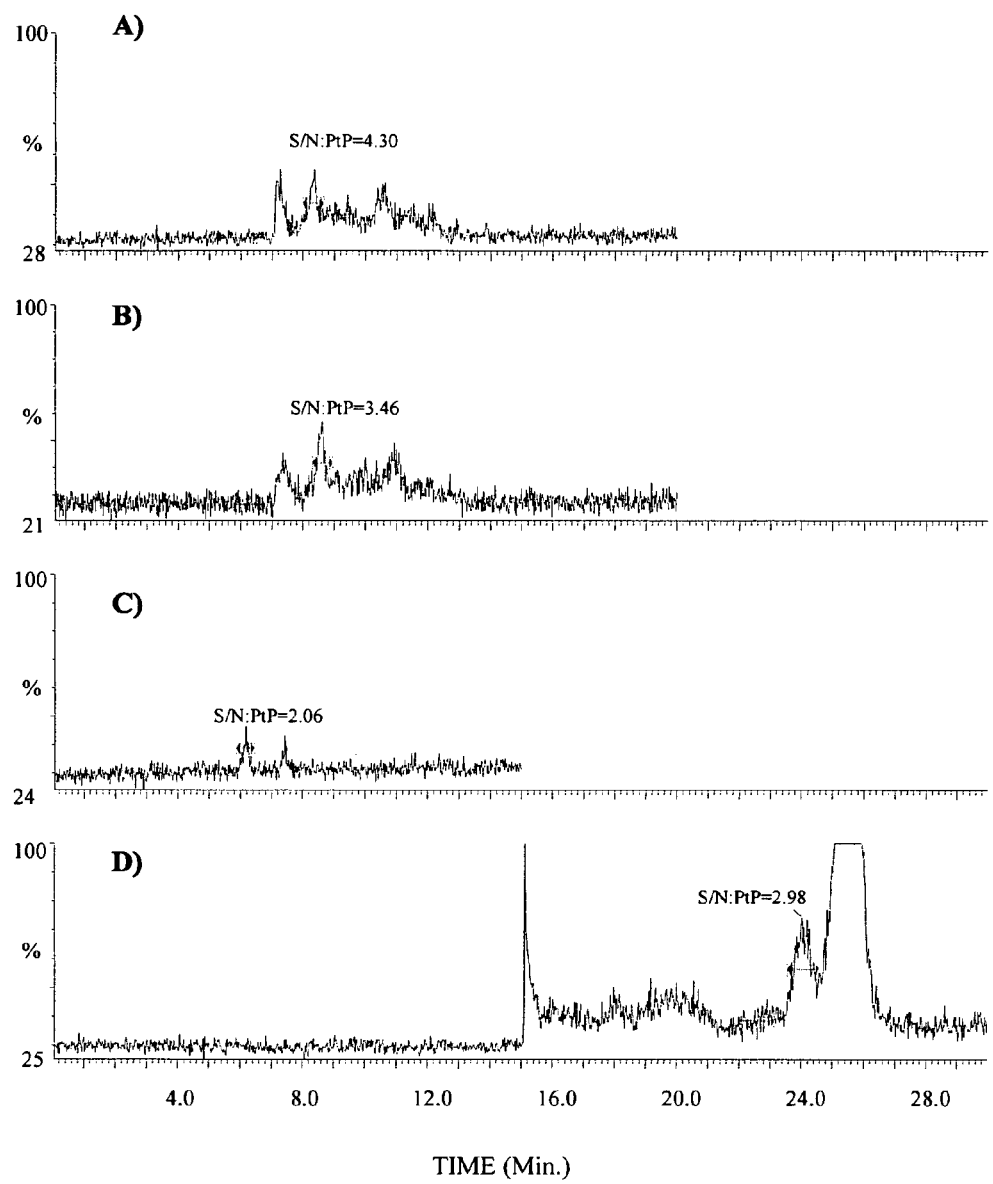
FIG. 6 illustrates an example of chromatograms in the calibration lower limits by the measurement method of the present invention and conventional method. A) is a chromatogram in the calibration lower limit by the measurement method of the present invention when 1 mL of rat plasma is used; B) is a chromatogram in the calibration lower limit by the measurement method of the present invention when 100 μL of rat plasma is used; C) is a chromatogram in the calibration lower limit when measured by PTAD derivatization (control); and D) is a chromatogram in the calibration lower limit by direct assay.

The calibration lower limit was estimated in the S/N ratio of approximately 3 to 5. As a result, the calibration lower limit was found to be 0.08 ng/mL in the measurement method of the present invention, indicating that the sensitivity was higher by 125 times as compared to direct assay (10 ng/mL) shown in COMPARATIVE EXAMPLE 4-1 and by 12.5 times as compared to measurement (1 ng/mL) by derivatization with PTAD shown in COMPARATIVE EXAMPLE 4-2. Using 1 mL of rat plasma, the calibration lower limit was estimated as described above. As a result, the calibration lower limit in the measurement method of the present invention was found to be 0.01 ng/mL. An example of chromatograms in the calibration lower limits is shown in FIG. 6.

(3) Study of Specificity

Chromatograms for the calibration blank (0 ng/mL) used in the first paragraph of (2) described above and the calibration lower limit (0.08 ng/mL) were compared. As a result, any peak interfering the measurement of ALF-FMTAD and $d_4$-ALF-FMTAD was not noted, or no interfering peak in the elution time of ALF-FMTAD was observed with the calibration blank sample, either.

(4) Study of the Range and Linearity of Calibration Curves

The samples used in the first paragraph of (2) described above were monitored, respectively, for 3 days to determine the peak area ratio for analyte versus I.S. In relation to the added concentration, the calibration curve was produced by the method of least squares ($1/y^2$ weighting) to determine a correlation coefficient (r) and trueness of the inverse value at each concentration. Based on the calibration curve and the peak area ratio of each sample, the measured value was determined in ng/mL unit by 3 effective digits. In derivatization with FMTAD, two isomers (6R/6S) were formed. The peak showing a larger S/N ratio was selected (retention time (R.T.) of about 8.8 mins.) and quantification was carried out.

Figure 7:
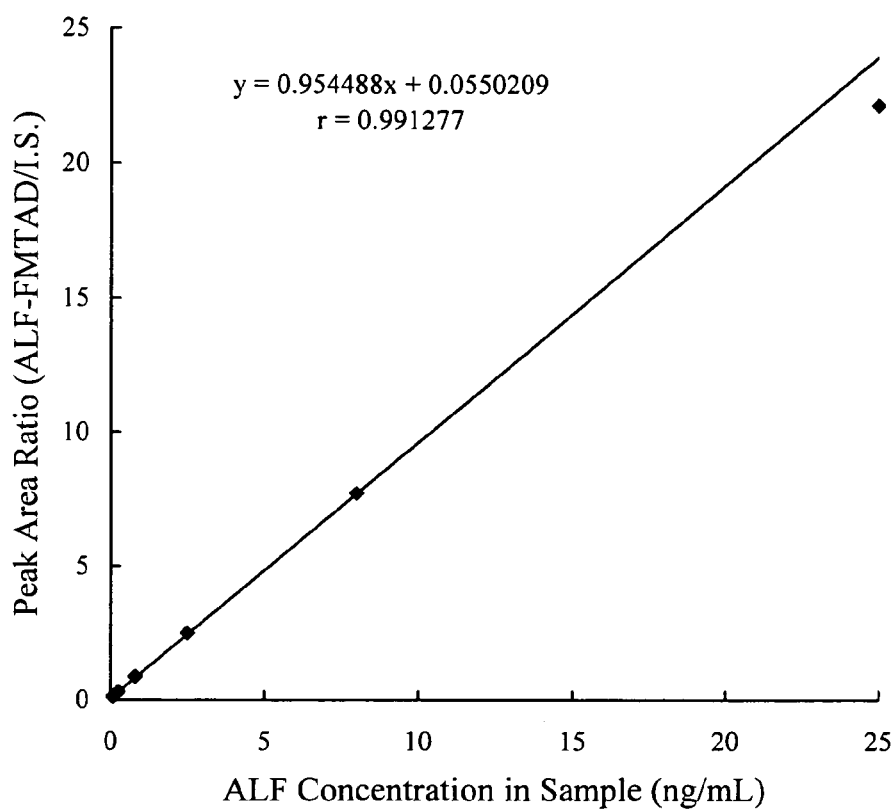
FIG. 7 illustrates an example of typical graphs showing the calibration curve for the measurement method of the present invention by ALF-FMTAD.

The results of calibration curves prepared for 3 days are shown in TABLE 3 and its typical graph is shown in FIG. 7.

TABLE 3

| Added Concentration (ng/mL) | Day 1 Found (ng/mL) | Day 1 Accuracy (%) | Day 2 Found (ng/mL) | Day 2 Accuracy (%) | Day 3 Found (ng/mL) | Day 3 Accuracy (%) |
|---|---|---|---|---|---|---|
| 0.08 | 0.0769 | −3.9 | 0.0790 | −1.3 | 0.0812 | 1.5 |
| 0.25 | 0.260 | 4.0 | 0.251 | 0.4 | 0.240 | −4.0 |
| 0.8 | 0.858 | 7.2 | 0.879 | 9.9 | 0.830 | 3.7 |
| 2.5 | 2.55 | 2.0 | 2.4 | −2.4 | 2.58 | 3.2 |
| 8 | 8.01 | 0.1 | 8.12 | 1.5 | 7.70 | −3.8 |
| 25 | 23.1 | −7.6 | 23.6 | −5.6 | 25.1 | 0.4 |

Linear regression equation:
Day 1   y = 0.954488x + 0.0550209   r = 0.991277 ($1/y^2$ weighting)
Day 2   y = 1.15772x + 0.0282662   r = 0.995203 ($1/y^2$ weighting)
Day 3   y = 1.05255x + 0.0404921   r = 0.999741 ($1/y^2$ weighting)

The correlation coefficients (r) of the calibration curves were 0.991277 to 0.999741 ($1/y^2$ weighting) in the range of 0.08 to 25 ng/mL and the accuracies of back calculated concentrations ranged from −7.6 to 9.9%, indicating a good linearity.

(5) Study of Within-Run Reproducibility

By adding ALF to rat blank plasma (100 μL) as in the first paragraph of (2) described above, the samples of 0.08, 0.25, 2.5 and 25 ng/mL were prepared for within-run reproducibility, treated and monitored, respectively. The samples were monitored daily for 3 days in n=5 at the respective concentrations to find coefficients of variation (hereinafter CV values) and trueness for every monitoring. The CV values and trueness were calculated by the following equations.

CV value=(found standard deviation/found mean value)×100(%)

Accuracy={(found mean value−theoretical value)/theoretical value}×100(%)

An example of the results is shown in TABLE 4.

TABLE 4

| Added Concentration (ng/mL) | Found (ng/mL) | Mean ± SD (ng/mL) | CV (%) | Accuracy (%) |
|---|---|---|---|---|
| Day 1 | | | | |
| 0.08 | 0.0675 | 0.0659 ± 0.0094 | 14.3 | −17.6 |
| | 0.0593 | | | |
| | 0.0795 | | | |
| | 0.0551 | | | |
| | 0.0679 | | | |
| 0.25 | 0.274 | 0.282 ± 0.039 | 13.8 | 12.8 |
| | 0.295 | | | |
| | 0.319 | | | |
| | 0.219 | | | |
| | 0.304 | | | |
| 2.5 | 2.75 | 2.71 ± 0.08 | 3.0 | 8.4 |
| | 2.70 | | | |
| | 2.57 | | | |
| | 2.77 | | | |
| | 2.77 | | | |
| 25 | 24.6 | 23.4 ± 1.5 | 6.4 | −6.4 |
| | 24.6 | | | |
| | 21.7 | | | |
| | 24.1 | | | |
| | 21.9 | | | |
| Day 2 | | | | |
| 0.08 | 0.0878 | 0.0854 ± 0.0104 | 12.2 | 6.8 |
| | 0.0949 | | | |
| | 0.0727 | | | |
| | 0.0763 | | | |
| | 0.0951 | | | |
| 0.25 | 0.263 | 0.267 ± 0.015 | 5.6 | 6.8 |
| | 0.256 | | | |
| | 0.275 | | | |
| | 0.290 | | | |
| | 0.252 | | | |
| 2.5 | 2.75 | 2.33 ± 0.33 | 14.2 | −6.8 |
| | 1.98 | | | |
| | 2.06 | | | |
| | 2.30 | | | |
| | 2.58 | | | |
| 25 | 24.8 | 25.2 ± 1.0 | 4.0 | 0.8 |
| | 24.5 | | | |
| | 26.8 | | | |
| | 25.6 | | | |
| | 24.5 | | | |
| Day 3 | | | | |
| 0.08 | 0.101 | 0.0799 ± 0.0149 | 18.6 | −0.1 |
| | 0.0827 | | | |
| | 0.0683 | | | |

TABLE 4-continued

| Added Concentration (ng/mL) | Found (ng/mL) | Mean ± SD (ng/mL) | CV (%) | Accuracy (%) |
|---|---|---|---|---|
| | 0.0844 | | | |
| | 0.0632 | | | |
| 0.25 | 0.270 | 0.256 ± 0.025 | 9.8 | 2.4 |
| | 0.267 | | | |
| | 0.282 | | | |
| | 0.221 | | | |
| | 0.240 | | | |
| 2.5 | 2.68 | 2.58 ± 0.16 | 6.2 | 3.2 |
| | 2.45 | | | |
| | 2.56 | | | |
| | 2.41 | | | |
| | 2.79 | | | |
| 25 | 25.3 | 24.9 ± 2.3 | 9.2 | −0.4 |
| | 22.8 | | | |
| | 23.0 | | | |
| | 24.8 | | | |
| | 28.5 | | | |

The CV values at the respective concentrations were 15% or less (20% or less in the lower limit of quantification) and the trueness was within ±15% (within ±20% in the lower limit of quantification), showing a good precision and trueness.

(6) Study of Between-Run Reproducibility

Based on the measurement results in (5) described above, the CV values and trueness over the entire 3 days were determined in a similar manner.

An example of the results is shown in TABLE 5.

TABLE 5

| Added Conc (ng/mL) | Found (ng/mL) | Mean ± SD (ng/mL) | CV (%) | Accuracy (%) |
|---|---|---|---|---|
| 0.08 | 0.0675 | 0.0770 ± 0.0138 | 17.9 | −3.8 |
| | 0.0593 | | | |
| | 0.0795 | | | |
| | 0.0551 | | | |
| | 0.0679 | | | |
| | 0.0878 | | | |
| | 0.0949 | | | |
| | 0.0727 | | | |
| | 0.0763 | | | |
| | 0.0951 | | | |
| | 0.101 | | | |
| | 0.0827 | | | |
| | 0.0683 | | | |
| | 0.0844 | | | |
| | 0.0632 | | | |
| 0.25 | 0.274 | 0.268 ± 0.028 | 10.4 | 7.2 |
| | 0.295 | | | |
| | 0.319 | | | |
| | 0.219 | | | |
| | 0.304 | | | |
| | 0.263 | | | |
| | 0.256 | | | |
| | 0.275 | | | |
| | 0.290 | | | |
| | 0.252 | | | |
| | 0.270 | | | |
| | 0.267 | | | |
| | 0.282 | | | |
| | 0.221 | | | |
| | 0.240 | | | |
| 2.5 | 2.75 | 2.54 ± 0.26 | 10.2 | 1.6 |
| | 2.70 | | | |
| | 2.57 | | | |
| | 2.77 | | | |

TABLE 5-continued

| Added Conc (ng/mL) | Found (ng/mL) | Mean ± SD (ng/mL) | CV (%) | Accuracy (%) |
|---|---|---|---|---|
| | 2.77 | | | |
| | 2.75 | | | |
| | 1.98 | | | |
| | 2.06 | | | |
| | 2.30 | | | |
| | 2.58 | | | |
| | 2.68 | | | |
| | 2.45 | | | |
| | 2.56 | | | |
| | 2.41 | | | |
| | 2.79 | | | |
| 25 | 24.6 | 24.5 ± 1.8 | 7.3 | −2.0 |
| | 24.6 | | | |
| | 21.7 | | | |
| | 24.1 | | | |
| | 21.9 | | | |
| | 24.8 | | | |
| | 24.5 | | | |
| | 26.8 | | | |
| | 25.6 | | | |
| | 24.5 | | | |
| | 25.3 | | | |
| | 22.8 | | | |
| | 23.0 | | | |
| | 24.8 | | | |
| | 28.5 | | | |

The CV values at the respective concentrations were 15% or less (20% or less in the lower limit of quantification) and the trueness was within ±15% (within ±20% in the lower limit of quantification), showing a good precision and trueness.

(7) Study of Recovery Rate

The samples for within-run reproducibility used in (5) above were utilized as samples for recovery rates. As control samples for calculation of the recovery rates (reference samples), 100 μL each of ALF-FMTAD with 0.145, 0.436, 4.36 and 43.6 ng/mL was dispensed to the pre-treated rat blank plasma to prepare two samples for each. By monitoring each sample, the recovery rate of ALF was determined by comparing the average peak area of the reference sample with the analyte peak area when the average peak area was made 100%.

Recovery rate=(peak area of sample for recovery rate/average peak area of reference sample)× 100(%)

An example of the results is shown in TABLE 6. The recovery rates were all efficient enough for practical use.

TABLE 6

| Added concentration (ng/mL) | Peak area of analyte | Peak area of reference sample | Recovery rate (%) | Average (%) | SD |
|---|---|---|---|---|---|
| 0.08 | 70 | 137 | 53.8 | 37.7 | 11.6 |
| | 51 | 123 | 39.2 | | |
| | 33 | | 25.4 | | |
| | 55 | | 42.3 | | |
| | 36 | | 27.7 | | |
| 0.25 | 148 | 239 | 44.2 | 39.1 | 8.0 |
| | 149 | 431 | 44.5 | | |
| | 85 | | 25.4 | | |
| | 129 | | 38.5 | | |
| | 143 | | 42.7 | | |

TABLE 6-continued

| Added concentration (ng/mL) | Peak area of analyte | Peak area of reference sample | Recovery rate (%) | Average (%) | SD |
|---|---|---|---|---|---|
| 2.5 | 1193 | 3127 | 40.1 | 41.2 | 9.5 |
|  | 1313 | 2828 | 44.1 |  |  |
|  | 757 |  | 25.4 |  |  |
|  | 1394 |  | 46.8 |  |  |
|  | 1474 |  | 49.5 |  |  |
| 25 | 5207 | 22412 | 20.7 | 24.5 | 4.8 |
|  | 5406 | 27884 | 21.5 |  |  |
|  | 5323 |  | 21.2 |  |  |
|  | 7820 |  | 31.1 |  |  |
|  | 7075 |  | 28.1 |  |  |

(7) Study of Derivatization Rate

The samples for within-run reproducibility used in (5) above were utilized as samples for derivatization rate. After protein precipitation with ethanol, solid phase extraction with a solid phase extraction cartridge (Bond Elut SI, 3 cc, 500 mg: manufactured by Varian SPP) followed by adding ALF-FMTAD to rat blank plasma added with FMTAD, two samples for each were prepared as control samples for calculating derivatization rates (reference samples). Each sample was monitored and the derivatization rate of ALF was determined by comparing the average peak area of the reference sample with the analyte peak area when the average peak area was made 100%.

Derivatization rate=(peak area of sample for derivatization rate/average peak area of reference sample)×100(%)

An example of the results is shown in TABLE 7. The derivatization rates were all efficient enough for practical use.

TABLE 7

| Added concentration (ng/mL) | Peak area of analyte | Peak area of reference sample | Derivatization rate (%) | Average (%) |
|---|---|---|---|---|
| 0.08 | 99 | 92 | 114.5 | 89.6 |
|  | 56 | 81 | 64.7 |  |
| 0.25 | 191 | 338 | 52.9 | 54.3 |
|  | 201 | 384 | 55.7 |  |
| 2.5 | 1734 | 3023 | 57.3 | 46.3 |
|  | 1069 | 3034 | 35.3 |  |
| 25 | 11141 | 26204 | 45.1 | 45.3 |
|  | 11239 | 23215 | 45.5 |  |

(8) Study of Stability in a Sample Cooler

By adding ALF to rat blank plasma (100 μL) as in the first paragraph of (2) described above, the samples of 0.08, 0.25, 2.5 and 25 ng/mL were prepared, treated and monitored, respectively, to examine stability. A variation rate was calculated by the following equation at each concentration in n=3, based on the found value on the day when the sample was prepared (Initial Value) and the found value after storage in a sample cooler at 5° C. for 24 hours (Post Value).

Variation rate={mean Post Value/mean Initial Value}×100(%)

In analysis of the variation rate, any large variation was not observed at any concentration, indicating that any problem was not noted in stability.

Example 4-2

Determination of ED-71 in Rat Plasma by Derivatization with FMTAD

Using LC/ESI-MS/MS, ED-71 in rat plasma was measured by derivatization with FMTAD in a manner similar to EXAMPLE 4-1 (2), first paragraph, except that ED-71 was used as a vitamin D compound. Conditions for the measurement are shown in TABLE 8.

TABLE 8

Conditions for measurement of ED-71-FMTAD:

| | |
|---|---|
| Column: | Capcell Pak C18 UG-120 (5 μm, 150 × 2.0 mm i.d.) |
| Mobile phase: | Solution A: 10 mmol/L ammonium acetate Solution B: acetonitrile (A: 45%, B: 55%) |
| Column temperature: | 30° C. |
| Flow rate: | 0.2 mL/min. |
| Ionization mode: | ESI (+) |
| Capillary voltage: | 1.0 kV |
| Cone Voltage: | 72 V |
| Source block temperature: | 150° C. |
| Desolvator temperature: | 450° C. |
| Collision energy: | 52 eV |
| Conditions for MRM (Multiple Reaction Monitoring): | |

ED-71-FMTAD: m/z 787 $[M]^+$ > 199 $[M-C_{33}H_{50}O_7N_3]^+$
$d_6$-ED-71-FMTAD: m/z 793 $[M]^+$ > 199 $[M-C_{33}H_{44}D_6O_7N_3]^+$

The calibration lower limit was estimated in the S/N ratio of about 3, and was 0.25 ng/mL in the measurement method of the present invention.

Example 4-3

Determination of the Compound Described in EXAMPLE 6 of WO 02/13832 (Compound A) in Rat Plasma by Derivatization with FMTAD Using LC/ESI-MS/MS, the compound described in EXAMPLE 6 of WO 02/13832 (Compound A) in rat plasma was measured by derivatization with FMTAD in a manner similar to EXAMPLE 3-2, first paragraph, except that Compound A was used in place of ED-71. Conditions for the measurement are shown in TABLE 9.

TABLE 9

Conditions for measurement of Compound A-FMTAD:

| | |
|---|---|
| Column: | Capcell Pak C18 UG-120 (5 μm, 150 × 2.0 mm i.d.) |
| Mobile phase: | Solution A: 10 mmol/L ammonium acetate Solution B: acetonitrile (A: 35%, B: 65%) |
| Column temperature: | 30° C. |
| Flow rate: | 0.2 mL/min. |
| Ionization mode: | ESI (+) |
| Capillary voltage: | 1.0 kV |
| Cone Voltage: | 65 V |
| Source block temperature: | 150° C. |
| Desolvator temperature: | 450° C. |
| Collision energy: | 55 eV |
| Conditions for MRM (Multiple Reaction Monitoring): | |

Compound A-FMTAD: m/z 749 $[M]^+$ > 199 $[M-C_{32}H_{44}O_5N_3]^+$

The calibration lower limit was estimated in the S/N ratio of about 3 and found to be 0.25 ng/mL in the measurement method of the present invention.

Comparative Example 4-1

Direct Assay of Alfacalcidol (ALF) in Rat Plasma without Derivatization

Alfacalcidol (ALF) was added to rat blank plasma as in EXAMPLE 4-1 (2) to prepare samples for generating calibration curves of 0, 1, 3, 10, 30, 100, 300 and 1000 ng/mL. After 20 μL of 400 ng/mL $d_4$-ALF was added as internal standard (I.S.) to 100 μL of the sample at each concentration, the sample was subjected to protein precipitation with ethanol and then solid phase extraction with a solid phase extraction cartridge (Bond Elut SI, 3 cc, 500 mg: manufactured by Varian SPP). After evaporation to dryness in nitrogen, the residue was dissolved in 40 μL of the mobile phase and 10 μL of the solution was injected into LC/ESI-MS/MS. Conditions for measurement are shown in TABLE 10.

TABLE 10

Conditions for measurement of ALF:

| | |
|---|---|
| Column: | Capcell Pak C18 UG-120 (5 μm, 150 × 2.0 mm i.d.) |
| Mobile phase: | Solution A: 10 mmol/L ammonium acetate<br>Solution B: menthol (A: 15%, B: 85%) |
| Column temperature: | 30° C. |
| Flow rate: | 0.2 mL/min. |
| Ionization mode: | ESI (+) |
| Capillary voltage: | 2.8 kV |
| Cone Voltage: | 15 V |
| Source block temperature: | 110° C. |
| Desolvator temperature: | 350° C. |
| Collision energy: | 10 eV |
| Conditions for MRM (Multiple Reaction Monitoring): | |

ALF: m/z 418 $[M + NH_4]^+$ > 383 $[M–H_2O + H]^+$
$d_4$-ALF-FMTAD: m/z 422 $[M + HN_4]^+$ > 387 $[M–H_2O + H]^+$

The calibration lower limit was estimated in the S/N ratio of about 3. As a result, the calibration lower limit was found to be 10 ng/mL in the direct assay. An example of chromatograms in the calibration lower limit is shown in FIG. 6, along with the results of EXAMPLE 4-1 (2) and the results of COMPARATIVE EXAMPLE 4-2 later described.

Comparative Example 4-2

Determination of Alfacalcidol (ALF) in Rat Plasma by Derivatization with PTAD (4-phenyl-1,2,4-triazoline-3,5-dione)

Alfacalcidol (ALF) was added to rat blank plasma as in EXAMPLE 4-1 (2) to prepare the samples of 0, 0.1, 0.3, 1, 3, 10, 30, 100 and 300 ng/mL for generating calibration curves. After 20 μL of 40 ng/mL $d_4$-ALF was added as internal standard (I.S.) to 100 μL of the sample at each concentration, the sample was subjected to protein precipitation with ethanol and then solid phase extraction with a solid phase extraction cartridge (Bond Elut SI, 3 cc, 500 mg: manufactured by Varian SPP), followed by derivatization with 4-phenyl-1,2,4-triazoline-3,5-dione (PTAD: manufactured by SIGMA) by the procedures described in the article (Biological Mass Spectrometry 1993; 22: 621–632, Journal of Chromatography 1993; 645: 115–123, etc.). Following the derivatization, the sample was evaporated to dryness in nitrogen and the residue was dissolved in 40 μL of a mobile phase and 10 μL of the solution was injected into LC/ESI-MS/MS. Conditions for measurement are shown in TABLE 11.

TABLE 11

Conditions for measurement of ALF-PTAD:

| | |
|---|---|
| Column: | Capcell Pak C18 UG-120 (5 μm, 150 × 2.0 mm i.d.) |
| Mobile phase: | Solution A: 10 mmol/L ammonium acetate/acetonitrile (1:1)<br>Solution B: 10 mmol/L ammonium acetate/acetonitrile (A: 35%, B: 65%) |
| Column temperature: | 40° C. |
| Flow rate: | 0.2 mL/min. |
| Ionization mode: | ESI (+) |
| Capillary voltage: | 3.5 kV |
| Cone Voltage: | 26 V |
| Source block temperature: | 110° C. |
| Desolvator temperature: | 350° C. |
| Collision energy: | 16 eV |
| Conditions for MRM (Multiple Reaction Monitoring): | |

ALF-PTAD: m/z 576 $[M + H]^+$ > 314 $[M–C_{19}H_{33}]^+$
$d_4$-ALF-PTAD: m/z 580 $[M + H]^+$ > 314 $[M–C_{19}H_{29}D_4]^+$

The calibration lower limit was estimated in the S/N ratio of about 2. As a result, the calibration lower limit was found to be 1 ng/mL when measured by derivatization with PTAD. An example of chromatograms in the calibration lower limit is shown in FIG. 6, along with the results of EXAMPLE 4-1 (2) and the results of COMPARATIVE EXAMPLE 4-1.

Example 4-4

Figure 8:
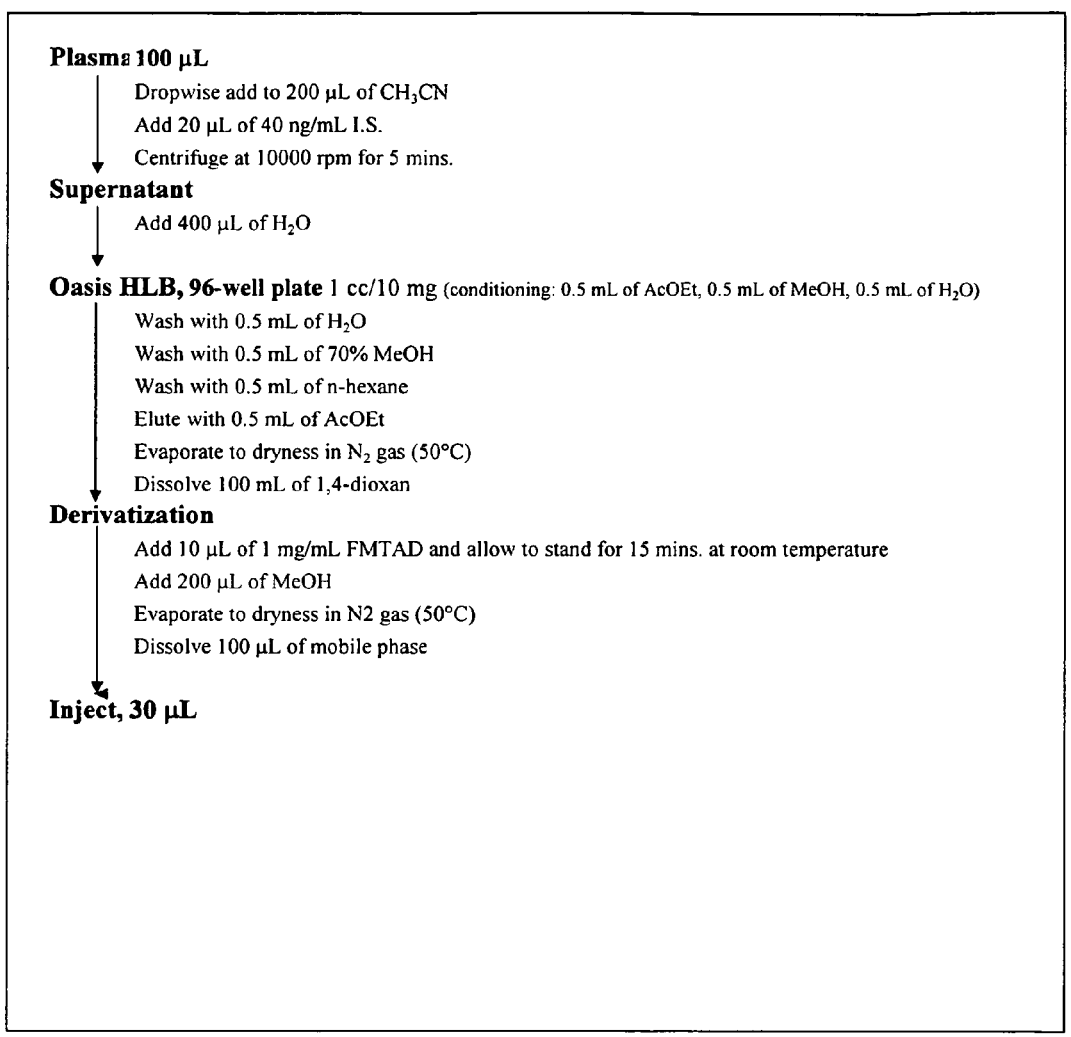
FIG. 8 is an example of specific treatment scheme for pre-treatment in the measurement method of the present invention when rat plasma is used as a sample, which simplifies the treatment procedures in FIG. 5.

Simplification of Pre-Treatment for Measurement of Vitamin D Derivatives in Biological Samples (1) Simplification of Pre-Treatment Conditions Pretreatment for the sample shown in FIG. 5 was simplified as follows. To alfacalcidol (ALF)-added rat blank plasma (100 μL), 20 μL of 40 ng/mL d4-ALF (I.S.) was added and after protein precipitation with acetonitrile, the mixture was subjected to solid phase extraction with a 96-well solid phase extraction cartridge (Oasis HLB 96-well plate, 1 cc, 10 mg: manufactured by Waters). After derivatization with FMTAD and evaporation to dryness in nitrogen, the product was dissolved in 100 μL of 10 mmols/L ammonium acetate/acetonitrile (23:77, v/v) and 30 μL of the solution was injected into LC/ESI-MS/MS using column switching. A specific scheme for treating the samples is shown in FIG. 8. Conditions for measurement of LC/ESI-MS/MS are shown in TABLE 12.

TABLE 12

Conditions (2) for measurement of ALF-FMTAD:

| | |
|---|---|
| Trapping column: | Cadenza CD-C18 (3 μm, 50 × 2.0 mm i.d.) |
| Column tempertaure: | room temperature |
| Analysis column: | Capcell Pak C18 UG-120 (5 μm, 150 × 2.0 mm i.d.) |
| Column temperature: | room temperature |
| Mobile phase 1: | Solution A: 10 mmol/L ammonium acetate<br>Solution B: acetonitrile |

TABLE 12-continued

| | |
|---|---|
| Flow rate: | 0.5 mL/min |
| | 0 min–5.20 mins. A: 23%, B: 77% |
| | 5.21 min–8.00 mins. A: 0%, B: 100% |
| | 8.01 min–14.00 mins. A: 23%, B: 77% |
| Mobile phase 2: | 10 mmol/L ammonium acetate/acetonitrile (10:90, v/v) |
| Flow rate: | 0.2 mL/min |
| Valve switching: | 0 min: Position 1 |
| | 4.25 min: Position 2 |
| | 5.2 min: Position 1 |
| Ionization mode: | ESI (+) |
| Capillary voltage: | 1.0 kV |
| Cone Voltage: | 70 V |
| Source block temperature: | 150° C. |
| Desolvator temperature: | 450° C. |
| Collision energy: | 46 eV |
| Conditions for MRM (Multiple Reaction Monitoring): | |

ALF-FMTAD: m/z 697 $[M]^+$ > 199 $[M-C_{29}H_{44}O_4N_3]^+$
$d_4$-ALF-FMTAD: m/z 701 $[M]^+$ > 199 $[M-C_{29}H_{40}D_4O_4N_4]^+$

Figure 9:
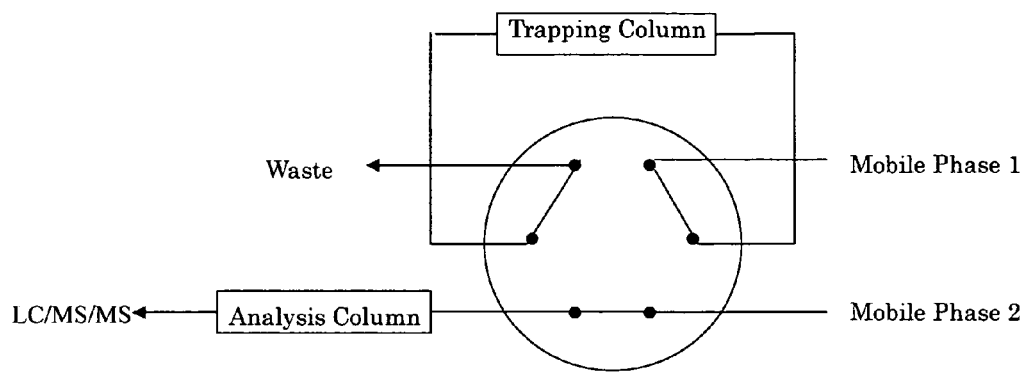
FIG. 9 illustrates column switching in the measurement method of the present invention.
Figure 9:
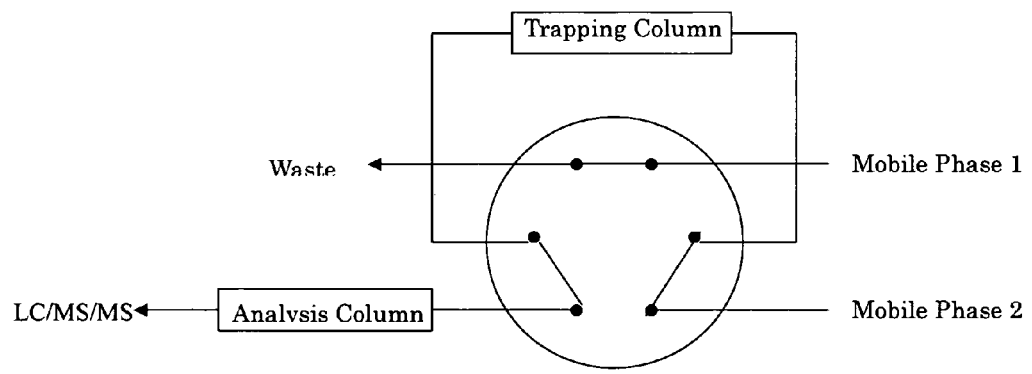

Column switching is illustrated in FIG. 9. In the derivatization reaction with FMTAD, two kinds of isomers (6R/6S) were formed. However, because the isomer initially eluted by HPLC had a higher S/N ratio, conditions for the column switching were set forth so as to pass the eluted fraction of only this isomer having a higher S/N ratio from the trapping column to the analytical column.

(2) Study of Calibration Range and Linearity

A solution of 100 ng/mL ALF in ethanol was diluted with rat blank plasma to prepare samples for generating calibration curves for 0, 0.05, 0.15, 0.5, 1.5, 5 and 15 ng/mL. Under the conditions shown in (1) above, 100 μL of the samples for generating calibration curves were treated for monitoring. The samples were monitored for 3 days. The peak area ratio for analyte versus I.S. was determined and in relation to the added concentration, the calibration curve was produced by the method of least squares (1/x weighting) to determine a correlation coefficient (r) and the accuracies of back calculated concentrations.

Figure 10:
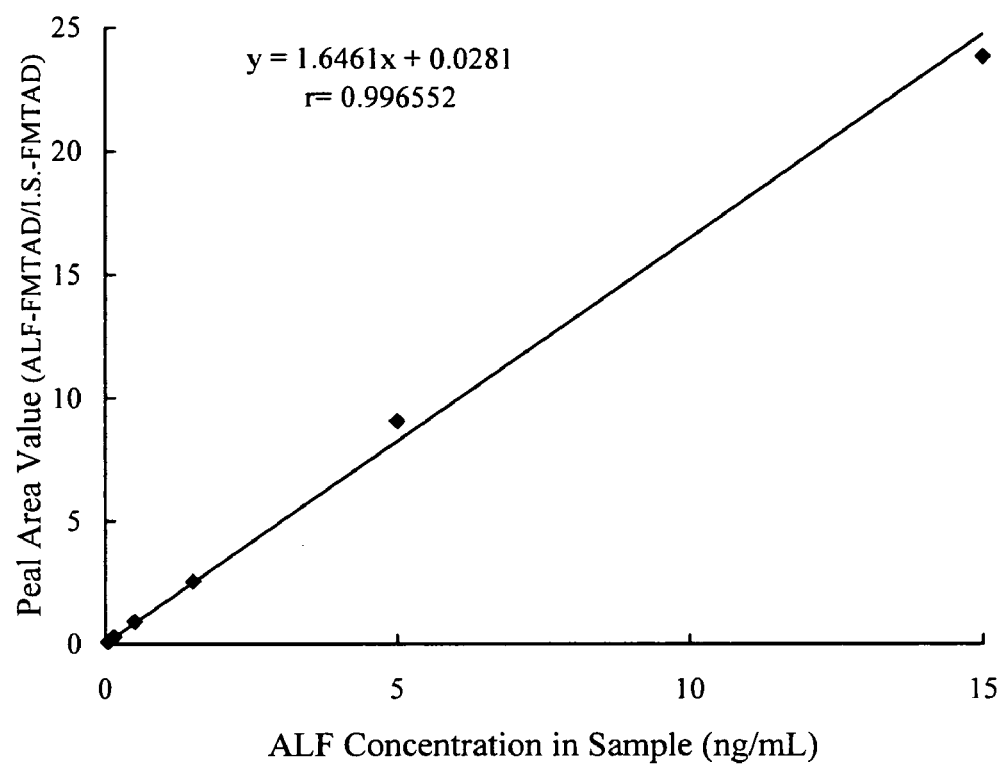
FIG. 10 shows an example of typical calibration curves for the measurement method of the present invention, when measured under the conditions of FIG. 8, FIG. 9 and TABLE 12.

The results of the calibration curves prepared over 3 days are shown in Table 3 and a typical graph is shown in FIG. 10.

TABLE 13

| Added Concentration (ng/mL) | Day 1 Found (ng/mL) | Day 1 Accuracy (%) | Day 2 Found (ng/mL) | Day 2 Accuracy (%) | Day 3 Found (ng/mL) | Day 3 Accuracy (%) |
|---|---|---|---|---|---|---|
| 0.05 | 0.0412 | −17.6 | 0.0497 | −0.7 | 0.0470 | −5.9 |
| 0.15 | 0.152 | 1.5 | 0.139 | −7.3 | 0.161 | 7.5 |
| 0.5 | 0.541 | 8.3 | 0.517 | 3.3 | 0.513 | 2.5 |
| 1.5 | 1.53 | 1.7 | 1.5 | 1.6 | 1.42 | −5.1 |
| 5 | 5.49 | 9.8 | 5.24 | 4.8 | 5.05 | 1.0 |
| 15 | 14.4 | −3.7 | 14.7 | −1.8 | 15.0 | 0.0 |

Linear regression equation:
Day 1   y = 1.64608x + 0.0281324   r = 0.996552 (1/x weighting)
Day 2   y = 1.63152x + 0.0257574   r = 0.999206 (1/x weighting)
Day 3   y = 1.58456x + 0.0548324   r = 0.999950 (1/x weighting)

The correlation coefficients (r) of the calibration curves were 0.996552 to 0.999950 in the range of 0.05 to 15 ng/mL and the trueness of inverse value at each concentration ranged from −17.6 to 9.8%, indicating a good linearity.

(3) Study of Within-Run Reproducibility

As in the first paragraph of (2) described above, the 100 ng/mL ALF ethanol solution was diluted with rat blank plasma to prepare the samples of 0.05, 0.15, 1.5 and 15 ng/mL for within-run reproducibility. The samples were treated for monitoring, respectively. The samples were monitored daily for 3 days in n=5 at the respective concentrations to find CV values and trueness for every monitoring. The results are shown in TABLE 14.

TABLE 14

| Added Concentration (ng/mL) | Found (ng/mL) | Mean ± SD (ng/mL) | CV (%) | Accuracy (%) |
|---|---|---|---|---|
| Day 1 | | | | |
| 0.05 | 0.0545 | 0.0546 ± 0.0021 | 3.8 | 9.2 |
| | 0.0546 | | | |
| | 0.0575 | | | |
| | 0.0517 | | | |
| | 0.0547 | | | |
| 0.15 | 0.175 | 0.160 ± 0.014 | 8.8 | 6.7 |
| | 0.158 | | | |
| | 0.166 | | | |
| | 0.137 | | | |
| | 0.167 | | | |
| 1.5 | 1.40 | 1.67 ± 0.16 | 9.6 | 11.3 |
| | 1.73 | | | |
| | 1.69 | | | |
| | 1.74 | | | |
| | 1.79 | | | |
| 15 | 15.6 | 16.8 ± 1.1 | 6.5 | 12.0 |
| | 16.7 | | | |
| | 16.0 | | | |
| | 17.0 | | | |
| | 18.5 | | | |
| Day 2 | | | | |
| 0.05 | 0.0526 | 0.0407 ± 0.0069 | 17.0 | −18.6 |
| | 0.0365 | | | |
| | 0.0357 | | | |
| | 0.0401 | | | |
| | 0.0384 | | | |
| 0.15 | 0.145 | 0.149 ± 0.010 | 6.7 | −0.7 |
| | 0.144 | | | |
| | 0.138 | | | |
| | 0.165 | | | |
| | 0.152 | | | |

TABLE 14-continued

| Added Concentration (ng/mL) | Found (ng/mL) | Mean ± SD (ng/mL) | CV (%) | Accuracy (%) |
|---|---|---|---|---|
| 1.5 | 1.67 | 1.68 ± 0.05 | 3.0 | 12.0 |
|  | 1.68 |  |  |  |
|  | 1.68 |  |  |  |
|  | 1.75 |  |  |  |
|  | 1.61 |  |  |  |
| 15 | 16.2 | 15.9 ± 0.2 | 1.3 | 6.0 |
|  | 16.0 |  |  |  |
|  | 15.6 |  |  |  |
|  | 15.9 |  |  |  |
|  | 15.7 |  |  |  |
| Day 3 |  |  |  |  |
| 0.05 | 0.042 | 0.0406 ± 0.0076 | 18.7 | −18.8 |
|  | 0.0392 |  |  |  |
|  | 0.0287 |  |  |  |
|  | 0.0442 |  |  |  |
|  | 0.0492 |  |  |  |
| 0.15 | 0.156 | 0.147 ± 0.014 | 9.5 | −2.0 |
|  | 0.156 |  |  |  |
|  | 0.122 |  |  |  |
|  | 0.152 |  |  |  |
|  | 0.151 |  |  |  |
| 1.5 | 1.63 | 1.61 ± 0.10 | 6.2 | 7.3 |
|  | 1.68 |  |  |  |
|  | 1.71 |  |  |  |
|  | 1.57 |  |  |  |
|  | 1.46 |  |  |  |
| 15 | 20.0 | 17.1 ± 1.8 | 10.5 | 14.0 |
|  | 15.7 |  |  |  |
|  | 15.4 |  |  |  |
|  | 17.8 |  |  |  |
|  | 16.8 |  |  |  |

On any of the days measured, the CV values at the respective concentrations were 15% or less (20% or less in the lower limit of quantification) and the trueness was within ±15% (within ±20% in the lower limit of quantification), showing a good precision and trueness.

(4) Study of Between-Run Reproducibility

Based on the results in (3) described above, the CV values and trueness over the entire 3 days were determined. The results are shown in TABLE 15.

TABLE 15

| Added Concentration (ng/mL) | Found (ng/mL) | Mean ± SD (ng/mL) | CV (%) | Accuracy (%) |
|---|---|---|---|---|
| 0.05 | 0.0545 | 0.0453 ± 0.088 | 19.4 | −9.4 |
|  | 0.0546 |  |  |  |
|  | 0.0575 |  |  |  |
|  | 0.0517 |  |  |  |
|  | 0.0547 |  |  |  |
|  | 0.0526 |  |  |  |
|  | 0.0365 |  |  |  |
|  | 0.0357 |  |  |  |
|  | 0.0401 |  |  |  |
|  | 0.0384 |  |  |  |
|  | 0.0418 |  |  |  |
|  | 0.0392 |  |  |  |
|  | 0.0287 |  |  |  |
|  | 0.0442 |  |  |  |
|  | 0.0492 |  |  |  |
| 0.15 | 0.175 | 0.152 ± 0.014 | 9.2 | 1.3 |
|  | 0.158 |  |  |  |
|  | 0.166 |  |  |  |
|  | 0.137 |  |  |  |
|  | 0.167 |  |  |  |

TABLE 15-continued

| Added Concentration (ng/mL) | Found (ng/mL) | Mean ± SD (ng/mL) | CV (%) | Accuracy (%) |
|---|---|---|---|---|
|  | 0.145 |  |  |  |
|  | 0.144 |  |  |  |
|  | 0.138 |  |  |  |
|  | 0.165 |  |  |  |
|  | 0.152 |  |  |  |
|  | 0.156 |  |  |  |
|  | 0.156 |  |  |  |
|  | 0.122 |  |  |  |
|  | 0.152 |  |  |  |
|  | 0.151 |  |  |  |
| 1.5 | 1.40 | 1.65 ± 0.11 | 6.7 | 10.0 |
|  | 1.73 |  |  |  |
|  | 1.69 |  |  |  |
|  | 1.74 |  |  |  |
|  | 1.79 |  |  |  |
|  | 1.67 |  |  |  |
|  | 1.68 |  |  |  |
|  | 1.68 |  |  |  |
|  | 1.75 |  |  |  |
|  | 1.61 |  |  |  |
|  | 1.63 |  |  |  |
|  | 1.68 |  |  |  |
|  | 1.71 |  |  |  |
|  | 1.57 |  |  |  |
|  | 1.46 |  |  |  |
| 15 | 15.6 | 16.6 ± 1.3 | 7.8 | 10.7 |
|  | 16.7 |  |  |  |
|  | 16.0 |  |  |  |
|  | 17.0 |  |  |  |
|  | 18.5 |  |  |  |
|  | 16.2 |  |  |  |
|  | 16.0 |  |  |  |
|  | 15.6 |  |  |  |
|  | 15.9 |  |  |  |
|  | 15.7 |  |  |  |
|  | 20.0 |  |  |  |
|  | 15.7 |  |  |  |
|  | 15.4 |  |  |  |
|  | 17.8 |  |  |  |
|  | 16.8 |  |  |  |

The CV values at the respective concentrations were 15% or less (20% or less in the lower limit of quantification) and the trueness was within ±15% (within ±20% in the lower limit of quantification), showing a good precision and trueness.

(5) Study of Recovery Rate

The samples for within-run reproducibility used in (3) above were utilized as samples for recovery rates. As control samples for calculating recovery rates (reference samples 1), 100 μL each of the ethanol solutions with 0.05, 0.15, 1.5 and 15 ng/mL ALF, which were prepared in (3) above, was dispensed to the pre-treated rat blank plasma to prepare three samples for each. After derivatization, the samples were monitored. When the average peak area of reference sample 1 was made 100%, the recovery rate of ALF was determined by comparing with the analyte peak area. The results are shown in TABLE 16. The recovery rates were all efficient enough for practical use. (%)

TABLE 16

| Added Conc. (ng/mL) | Recovery Rate (%) | Mean ± SD (%) | Derivetization Rate (%) | Mean ± SD (%) |
|---|---|---|---|---|
| 0.05 | 86.5 | 73.8 ± 8.8 | 65.5 | 50.5 ± 13.5 |
|  | 66.2 |  | 39.3 |  |
|  | 64.9 |  | 46.6 |  |
|  | 77.0 |  |  |  |
|  | 74.3 |  |  |  |
| 0.15 | 84.9 | 72.3 ± 12.3 | 58.7 | 56.8 ± 2.0 |
|  | 71.9 |  | 54.8 |  |
|  | 52.8 |  | 57.0 |  |
|  | 80.4 |  |  |  |
|  | 71.4 |  |  |  |
| 1.5 | 61.0 | 87.9 ± 15.9 | 68.6 | 60.7 ± 7.0 |
|  | 96.6 |  | 55.4 |  |
|  | 86.0 |  | 58.0 |  |
|  | 98.6 |  |  |  |
|  | 97.4 |  |  |  |
| 15 | 77.0 | 85.4 ± 7.8 | 74.2 | 65.5 ± 9.4 |
|  | 85.4 |  | 55.5 |  |
|  | 98.1 |  | 66.8 |  |
|  | 84.3 |  |  |  |
|  | 82.4 |  |  |  |

(6) Study of Derivatization Rate

The reference samples (1) prepared in (5) above were utilized as control samples for derivatization rates. As control samples for calculating the derivatization rates (reference samples 2), three samples for each were prepared by adding to the pre-treated and derivatized rat blank plasma 100 μL each of the ethanol solutions with 0.0436, 0.0871, 1.39 and 13.9 ng/mL ALF-FMTAD, and the samples were monitored. When the average peak area of the reference sample 2 was made 100%, the extraction efficiency of ALF was determined by comparing with the analyte peak area. The results are shown in TABLE 16. The derivatization rates were all efficient enough for practical use.

(7) Study of Specificity

Figure 11:
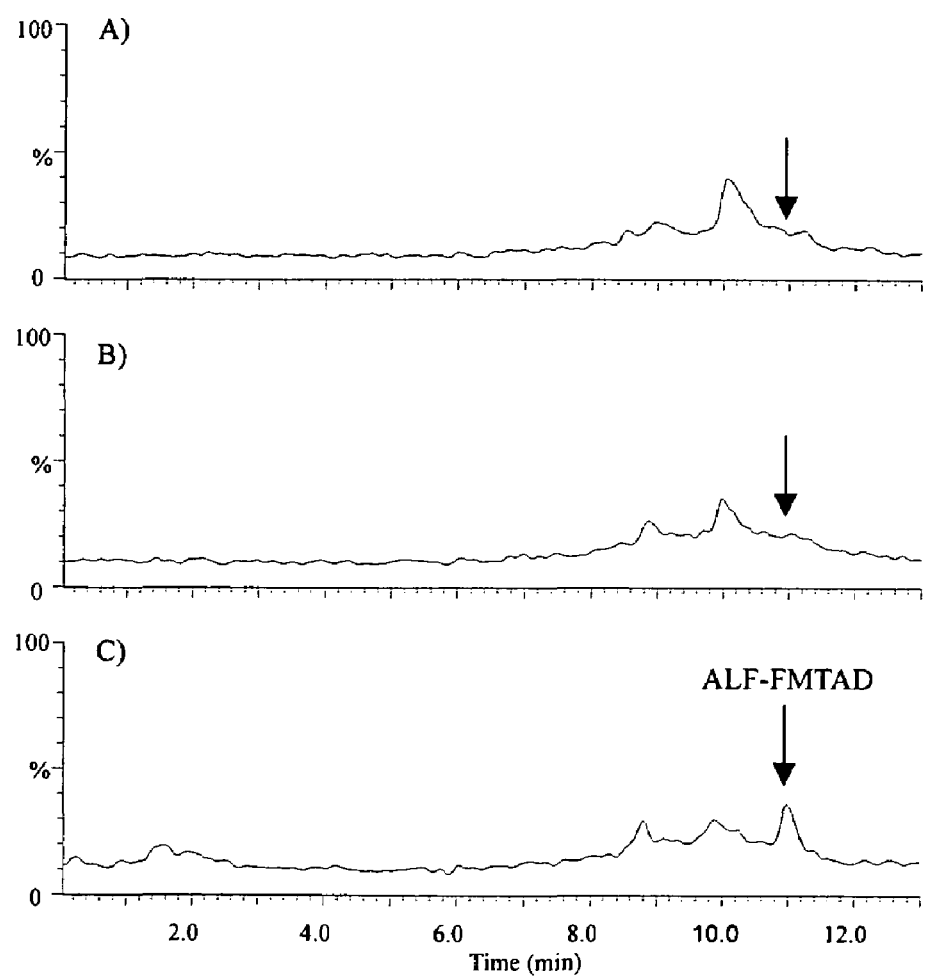
FIG. 11 illustrates chromatograms of ALF-FMTAD specificity in the measurement method of the present invention, when measured under the conditions of FIG. 8, FIG. 9 and TABLE 12. A) is a chromatogram of rat blank plasma, B) is a chromatogram of calibration blank (ALF: 0 ng/mL) and C) is a chromatogram of the calibration lower limit (ALF: 0.05 ng/mL).
Figure 12:
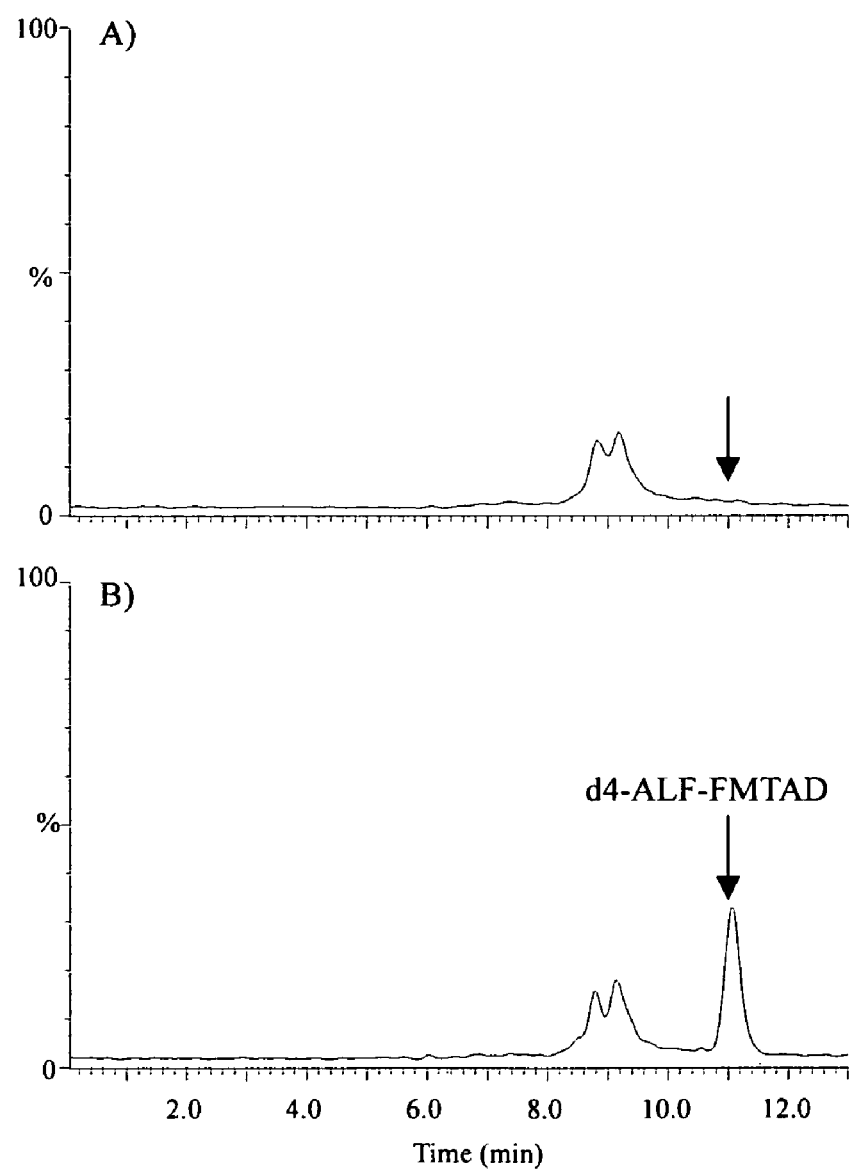
FIG. 12 illustrates chromatograms of $d_4$-ALF-FMTAD specificity in the measurement method of the present invention, when measured under the conditions of FIG. 8, FIG. 9 and TABLE 12. A) is a chromatogram of rat blank plasma.

Chromatograms for rat blank plasma, the calibration blank used in (2) above (0 ng/mL) described above and the calibration lower limit (0.05 ng/mL) were compared. The chromatogram of ALF-FMTAD is shown in FIG. 11 and the chromatogram of d4-ALF-FMTAD is shown in FIG. 12.

Any peak of interfering with the measurement of ALF-FMTAD and d4-ALF-FMTAD was not observed with rat blank plasma. Furthermore, any peak of interfering with the measurement of ALF-FMTAD was not observed with the calibration blank (0 ng/mL).

SUMMARY

As shown in EXAMPLES above, by simplifying the pre-treatment in the derivatization of vitamin D derivatives with FMTAD and adopting the LC/ESI-MS/MS techniques using column switching, the recovery rate could be improved and the lower limit of quantification could be made 0.05 ng/mL, resulting in a higher sensitivity. The method of the invention is an excellent quantification method in terms of the sensitivity, linearity and precision and considered to be efficiently applicable also to analysis of multiple samples.

As described above, the ferrocene compound of the present invention is reacted with a VD compound, and the combined compound of these compounds is subjected to LC/ESI-MS/MS, whereby the VD compound can be measured with a higher sensitivity than in conventional techniques. Furthermore, in the measurement of a VD compound having no hetero atom such as an ester bond, an ether bond, a thioether bond, an amide bond, etc. in the molecule (specifically, VD3, calcipotriol, 1α, 25(OH)$_2$D$_3$, ALF, falecalcitriol, EB1089, Compound A, etc. described above) which were measured with an insufficient sensitivity in conventional methods, the measurement method of the present invention is a high-sensitivity method which can achieve the sensitivity of higher even by several hundred times than in conventional methods. Accordingly, the high-sensitivity measurement method is applicable to all VD compounds, including not only VD compounds having hetero atoms such as an ester bond, an ether bond, a thioether bond, an amide bond, etc. (specifically, OCT, ED-71, etc. described above) but also VD compounds having no such hetero atom. Moreover, the method of measuring a VD compound is easily handled, since the reaction conditions require no heating or the like, as in the case of using ferrocenyl azide as a derivatization agent.

Furthermore, the ferrocene compound of the present invention is very useful as a derivatization agent in measuring a VD compound by LC/ESI-MS/MS, as described above.

The compound obtained, wherein the ferrocene compound and a VD compound have been combined with each other, is useful as, e.g., a reference standard in measuring a VD compound by LC/ESI-MS/MS.

What is claimed is:

1. A ferrocene compound represented by formula (1) below:

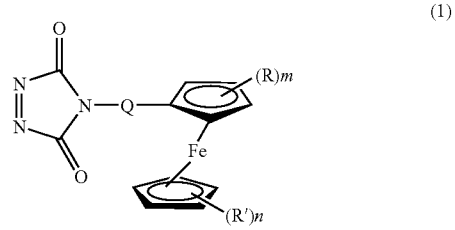

wherein Q represents a direct bond, alkylene or —W$_1$—X—W$_2$— (wherein W$_1$ represents alkylene or phenylene; W$_2$ represents alkylene; X represents —O—, —N(R$_a$)C(=O)—, —N(R$_a$)C(=O)NH—, —OC(=O)NH— or —N(R$_a$)OS(=O)—; and R$_a$ represents a lower alkyl group); each of R and R' independently represents a hydrogen atom, hydroxy group, nitro group, cyano group, halogen, optionally substituted lower alkyl group, optionally substituted lower alkenyl group, optionally substituted lower alkynyl group, optionally substituted lower alkoxy group, optionally substituted lower acyl group, optionally substituted carboxy group, or optionally substituted carbamoyl group; m represents an integer of 1 to 3; and n represents an integer of 1 to 4.

2. The ferrocene compound according to claim 1, wherein R and R' are a hydrogen atom.

3. The ferrocene compound according to claim 1, wherein Q represents a direct bond or alkylene.

4. The ferrocene compound according to claim 1, wherein Q is methylene.

5. The ferrocene compound according to claim 1, wherein Q is a direct bond.

6. The ferrocene compound according to claim 1, which is 4-(ferrocenylmethyl)-1,2,4-triazoline-3,5-dione or 4-ferrocenyl-1,2,4-triazoline-3,5-dione.

7. A reagent for measuring a triene structure, comprising the ferrocene compound according to claim 1.

8. The reagent according to claim 7, which further comprises a solvent capable of dissolving the ferrocene compound.

9. A combined compound of a ferrocene compound represented by formula (1) below, and a vitamin D compound:

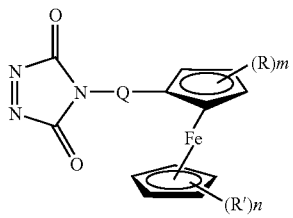

(1)

wherein Q represents a direct bond, alkylene or $-W_1-X-W_2-$ (wherein $W_1$ represents alkylene or phenylene; $W_2$ represents alkylene; X represents $-O-$, $-N(R_a)C(=O)-$, $-N(R_a)C(=O)NH-$, $-OC(=O)NH-$ or $-N(R_a)OS(=O)-$; and $R_a$ represents a lower alkyl group); each of R and R' independently represents a hydrogen atom, hydroxy group, nitro group, cyano group, halogen, optionally substituted lower alkyl group, optionally substituted lower alkenyl group, optionally substituted lower alkynyl group, optionally substituted lower alkoxy group, optionally substituted lower acyl group, optionally substituted carboxy group, or optionally substituted carbamoyl group; m represents an integer of 1 to 3; and n represents an integer of 1 to 4.

10. The compound according to claim 9, wherein the combined compound of the ferrocene compound and a vitamin D compound is a combined compound wherein the ferrocene compound and the vitamin D compound have been combined with each other through a covalent bond.

11. The compound according to claim 9, wherein the combined compound of the ferrocene compound and a vitamin D compound is a compound represented by formula (2):

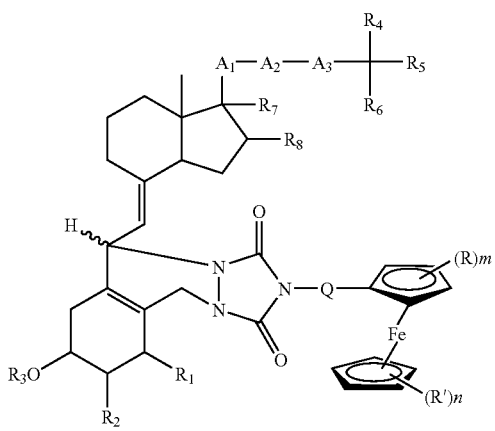

(2)

wherein each of $A_1$ and $A_3$ independently represents optionally substituted lower alkylene, optionally substituted lower alkenylene, or optionally substituted lower alkynylene; $A_2$ represents a direct bond, $-CH=CH-$, $-C\equiv C-$, $-O-$, $-S-$ or $-NH-$; $R_1$ represents a hydrogen atom or $-OR_9$ ($R_9$ represents a hydrogen atom or protecting group); $R_2$ represents a hydrogen atom, hydroxy group, halogen, optionally substituted lower alkyl group, optionally substituted lower alkenyl group, optionally substituted lower alkynyl group, optionally substituted lower alkoxy group or optionally substituted lower acyl group; $R_3$ represents a hydrogen atom or protecting group; each of $R_4$, $R_5$ and $R_6$ independently represents a hydrogen atom, hydroxy group, nitro group, cyano group, halogen, optionally substituted lower alkyl group, optionally substituted cycloalkyl group, optionally substituted lower alkenyl group, optionally substituted lower alkynyl group, optionally substituted lower alkoxy group, optionally substituted lower acyl group, optionally substituted carboxy group, optionally substituted carbamoyl group or optionally substituted amino group; each of $R_7$ and $R_8$ independently represents a hydrogen atom or hydroxy group, or, $R_7$ and $R_8$ are linked together to form a double bond; Q represents a direct bond, alkylene or $-W_1-X-W_2-$ (wherein $W_1$ represents alkylene or phenylene; $W_2$ represents alkylene; X represents $-O-$, $-N(R_a)C(=O)-$, $-N(R_a)C(=O)NH-$, $-OC(=O)NH-$ or $-N(R_a)OS(=O)-$, and $R_a$ represents a lower alkyl group); each of R and R' independently represents a hydrogen atom, hydroxy group, nitro group, cyano group, halogen, optionally substituted lower alkyl group, optionally substituted lower alkenyl group, optionally substituted lower alkynyl group, optionally substituted lower alkoxy group, optionally substituted lower acyl group, optionally substituted carboxy group or optionally substituted carbamoyl group; m represents an integer of 1 to 3; and n represents an integer of 1 to 4.

12. The compound according to claim 9, wherein $A_1$-$A_2$-$A_3$ represents $-CH(CH_3)-(CH_2)_3-$, $-CH(CH_3)-CH=CH-$ or $-CH(CH_3)-CH=CH-CH=CH-$; $R_1$ represents a hydrogen atom or hydroxy group; $R_2$ represents a hydrogen atom or hydroxypropoxy group; $R_3$ is a hydrogen atom; each of $R_4$, $R_5$ and $R_6$ independently represents a hydrogen atom, hydroxy group, lower alkyl group which may optionally be substituted with halogen, or lower cycloalkyl group which may optionally be substituted with halogen; $R_7$ and $R_8$ are a hydrogen atom, or, $R_7$ and $R_8$ are linked together to form a double bond.

13. The compound according to claim 9, wherein R and R' are a hydrogen atom.

14. The compound according to claim 9, wherein Q represents a direct bond or alkylene.

15. The compound according to claim 9, wherein Q is methylene.

16. The compound according to claim 9, wherein Q is a direct bond.

17. The compound according to claim 9, wherein the vitamin D compound is a vitamin $D_3$ compound.

18. A method of measuring a vitamin D compound contained in a sample, which comprises reacting a ferrocene compound represented by formula (1) below:

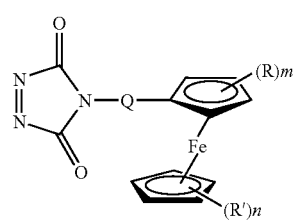

(1)

wherein Q represents a direct bond, alkylene or —W$_1$—X—W$_2$— (wherein W$_1$ represents alkylene or phenylene; W$_2$ represents alkylene; X represents —O—, —N(R$_a$)C(=O)—, —N(R$_a$)C(=O)NH—, —OC(=O)NH— or —N(R$_a$)OS(=O)—; and R$_a$ represents a lower alkyl group); each of R and R' independently represents a hydrogen atom, hydroxy group, nitro group, cyano group, halogen, optionally substituted lower alkyl group, optionally substituted lower alkenyl group, optionally substituted lower alkynyl group, optionally substituted lower alkoxy group, optionally substituted lower acyl group, optionally substituted carboxy group, or optionally substituted carbamoyl group; m represents an integer of 1 to 3; and n represents an integer of 1 to 4, with a vitamin D compound, and measuring the resulting combined compound of the ferrocene compound and the vitamin D compound by liquid chromatography/mass spectrometry (LC/MS).

19. The method of measuring a vitamin D compound according to claim 18, wherein the combined compound of the ferrocene compound and a vitamin D compound is a combined compound wherein the ferrocene compound and the vitamin D compound have been combined with each other through a covalent bond.

20. The method of measuring a vitamin D compound according to claim 18, wherein the combined compound of the ferrocene compound and a vitamin D compound is a compound represented by formula (2) below:

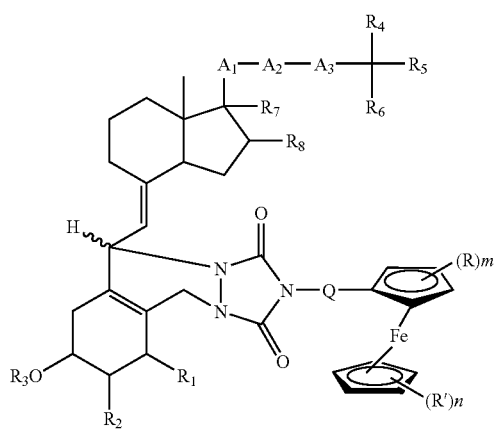

(2)

wherein each of A$_1$ and A$_3$ independently represents optionally substituted lower alkylene, optionally substituted lower alkenylene, or optionally substituted lower alkynylene; A$_2$ represents a direct bond, —CH=CH—, —C=C—, —O—, —S— or —NH—; R$_1$ represents a hydrogen atom or —OR$_9$ (R$_9$ represents a hydrogen atom or protecting group); R$_2$ represents a hydrogen atom, hydroxy group, halogen, optionally substituted lower alkyl group, optionally substituted lower alkenyl group, optionally substituted lower alkynyl group, optionally substituted lower alkoxy group or optionally substituted lower acyl group; R$_3$ represents a hydrogen atom or protecting group; each of R$_4$, R$_5$ and R$_6$ independently represents a hydrogen atom, hydroxy group, nitro group, cyano group, halogen, optionally substituted lower alkyl group, optionally substituted cycloalkyl group, optionally substituted lower alkenyl group, optionally substituted lower alkynyl group, optionally substituted lower alkoxy group, optionally substituted lower acyl group, optionally substituted carboxy group, optionally substituted carbamoyl group or optionally substituted amino group; each of R$_7$ and R$_8$ independently represents a hydrogen atom or hydroxy group, or, R$_7$ and R$_8$ are linked together to form a double bond; Q represents a direct bond, alkylene or —W$_1$—X—W$_2$— (wherein W$_1$ represents alkylene or phenylene; W$_2$ represents alkylene; X represents —O—, —N(R$_a$)C(=O)—, —N(R$_a$)C(=O)NH—, —OC(=O)NH— or —N(R$_a$)OS(=O)—, and R$_a$ represents a lower alkyl group); each of R and R' independently represents a hydrogen atom, hydroxy group, nitro group, cyano group, halogen, optionally substituted lower alkyl group, optionally substituted lower alkenyl group, optionally substituted lower alkynyl group, optionally substituted lower alkoxy group, optionally substituted lower acyl group, optionally substituted carboxy group or optionally substituted carbamoyl group; m represents an integer of 1 to 3; and n represents an integer of 1 to 4.

21. The method of measuring a vitamin D compound according to claim 18, wherein, in the ferrocene compound and the combined compound of the ferrocene compound and a vitamin D compound, A$_1$-A$_2$-A$_3$ represents —CH(CH$_3$)—(CH$_2$)$_3$—, —CH(CH$_3$)—CH=CH— or —CH(CH$_3$)—CH=CH—CH=CH—; R$_1$ represents a hydrogen atom or hydroxy group; R$_2$ represents a hydrogen atom or hydroxypropoxy group; R$_3$ is a hydrogen atom; each of R$_4$, R$_5$ and R$_6$ independently represents a hydrogen atom, hydroxy group, lower alkyl group which may optionally be substituted with a halogen, or a lower cycloalkyl group which may optionally be substituted with a halogen; R$_7$ and R$_8$ are a hydrogen atom, or, R$_7$ and R$_8$ are linked together to form a double bond.

22. The method of measuring a vitamin D compound according to claim 18, wherein, in the ferrocene compound and the combined compound of the ferrocene compound and a vitamin D compound, R and R' are a hydrogen atom.

23. The method of measuring a vitamin D compound according to claim 18, wherein, in the ferrocene compound and the combined compound of the ferrocene compound and a vitamin D compound, Q represents a direct bond or alkylene.

24. The method of measuring a vitamin D compound according to claim 18, wherein, in the ferrocene compound and the combined compound of the ferrocene compound and a vitamin D compound, Q is methylene.

25. The method of measuring a vitamin D compound according to claim 18, wherein, in the ferrocene compound and the combined compound of the ferrocene compound and a vitamin D compound, Q is a direct bond.

26. The method of measuring a vitamin D compound according to claim 18, wherein the vitamin D compound in a sample is a vitamin D$_3$ compound.

27. The method of measuring a vitamin D compound according to claim 18, wherein the sample is taken from a living body.

28. The method of measuring a vitamin D compound according to claim 18, wherein the liquid chromatography/mass spectrometry (LC/MS) is liquid chromatography/electrospray ionization-mass spectrometry/mass spectrometry (LC/ESI-MS/MS).

* * * * *